US012100273B2

(12) United States Patent
Carlson

(10) Patent No.: US 12,100,273 B2
(45) Date of Patent: *Sep. 24, 2024

(54) METHOD AND SYSTEM FOR USING DATA PACKET TRANSMISSION TO DETERMINE COMPLIANCE WITH PROTOCOLS

(71) Applicant: GOJO Industries, Inc., Akron, OH (US)

(72) Inventor: Grant Benjamin Carlson, Hammondsport, NY (US)

(73) Assignee: GOJO Industries, Inc., Akron, OH (US)

( * ) Notice: Subject to any disclaimer, the term of this patent is extended or adjusted under 35 U.S.C. 154(b) by 18 days.

This patent is subject to a terminal disclaimer.

(21) Appl. No.: 18/128,544

(22) Filed: Mar. 30, 2023

(65) Prior Publication Data
US 2023/0237888 A1 Jul. 27, 2023

Related U.S. Application Data

(63) Continuation of application No. 16/581,623, filed on Sep. 24, 2019, now Pat. No. 11,640,753.

(60) Provisional application No. 62/735,443, filed on Sep. 24, 2018.

(51) Int. Cl.
| | | |
|---|---|---|
| *G08B 23/00* | (2006.01) | |
| *G08B 13/19* | (2006.01) | |
| *G08B 21/22* | (2006.01) | |
| *G08B 21/24* | (2006.01) | |

(Continued)

(52) U.S. Cl.
CPC ............. *G08B 13/19* (2013.01); *G08B 21/22* (2013.01); *G08B 21/245* (2013.01); *G16H 40/20* (2018.01); *H04L 69/28* (2013.01)

(58) Field of Classification Search
CPC ...... G08B 13/19; G08B 21/22; G08B 21/245; G16H 40/20; H04L 69/28; H04L 67/52; H04W 4/025
USPC ..... 709/224; 340/573.1, 691.1, 693.1, 539.1, 340/539.11
See application file for complete search history.

(56) References Cited

U.S. PATENT DOCUMENTS

| | | | |
|---|---|---|---|
| 6,727,818 B1 * | 4/2004 | Wildman ............... | G16H 40/20 340/567 |
| 11,640,753 B2 * | 5/2023 | Carlson ................. | H04W 4/025 709/224 |

(Continued)

*Primary Examiner* — Anh V La
(74) *Attorney, Agent, or Firm* — Cooper Legal Group, LLC

(57) ABSTRACT

One or more computing devices, systems, and/or methods for determining a time-length of an action are provided. For example, a first event may be detected. Responsive to detecting the first event, a first inquiry may be transmitted in a first direction, using a first device. The first inquiry may be received by a second device. Responsive to receiving the first inquiry, a first reply data packet, comprising an identification number associated with the second device, may be transmitted, using the second device, to the first device. A second event may be detected. Responsive to detecting the second event, a second inquiry may be transmitted in a second direction, using a third device. The second inquiry may be received by the second device. Responsive to receiving the second inquiry, a second reply data packet, comprising the identification number, may be transmitted, using the second device, to the third device.

20 Claims, 18 Drawing Sheets

(51) Int. Cl.
*G16H 40/20* (2018.01)
*H04L 69/28* (2022.01)

(56) References Cited

U.S. PATENT DOCUMENTS

| | | | | |
|---|---|---|---|---|
| 2007/0197229 A1* | 8/2007 | Kalliola | ................... | G01S 3/46 |
| | | | | 455/456.1 |
| 2011/0121974 A1* | 5/2011 | Tenarvitz | ............. | G08B 21/245 |
| | | | | 340/10.1 |
| 2012/0112906 A1* | 5/2012 | Borke | ................... | G16H 40/20 |
| | | | | 340/539.13 |
| 2013/0187779 A1* | 7/2013 | Pokrajac | ................ | G08B 21/18 |
| | | | | 340/573.1 |
| 2014/0266732 A1* | 9/2014 | Barbeau | ................ | G16H 40/20 |
| | | | | 340/573.1 |

\* cited by examiner

METHOD AND SYSTEM FOR USING DATA PACKET TRANSMISSION TO DETERMINE COMPLIANCE WITH PROTOCOLS

RELATED APPLICATION

This application claims priority to and is a continuation of U.S. application Ser. No. 16/581,623, filed on Sep. 24, 2019, entitled "METHOD AND SYSTEM FOR USING DATA PACKET TRANSMISSION TO DETERMINE COMPLIANCE WITH PROTOCOLS", which claims the benefit of U.S. Provisional Application No. 62/735,443 filed on Sep. 24, 2018. U.S. application Ser. No. 16/581,623 and U.S. Provisional Application No. 62/735,443 are incorporated herein by reference in their entirety.

BACKGROUND

Many healthcare facilities and/or companies have a protocol for employees to follow. For example, the protocol may impose a time-limit within which employees are to interact with a dispense device after entering a room (e.g., a patient's room in a hospital).

SUMMARY

In accordance with the present disclosure, one or more computing devices and/or methods are provided. In an example, a system may comprise a first device associated with a first identification number. The first device may comprise a first sensor and a first transceiver. The first sensor may be configured to detect motion at a first location. The first sensor may be configured to activate the first transceiver responsive to detecting motion at the first location. The first transceiver may be configured to transmit a first inquiry in a first direction. The first transceiver may be configured to receive a first reply data packet, associated with the first inquiry, from a second device comprising a second transceiver. The first reply data packet may comprise a second identification number associated with the second device. The first transceiver may be configured to transmit a first message to a data processing station. The first message may comprise the first identification number and the second identification number. The system may comprise a third device associated with a third identification number. The third device may comprise a second sensor and a third transceiver. The second sensor may be configured to detect motion at a second location. The second sensor may be configured to activate the third transceiver responsive to detecting the motion at the second location. The third transceiver may be configured to transmit a second inquiry in a second direction. The third transceiver may be configured to receive a second reply data packet, associated with the second inquiry, from the second device. The second reply data packet may comprise the second identification number. The third transceiver may be configured to transmit a second message to the data processing station. The second message may comprise the second identification number and the third identification number.

In an example, a system may comprise a first device and a third device. The first device may be associated with a first identification number and may be configured to detect a first event. The first device may be configured to transmit a first inquiry in a first direction responsive to detecting the first event. The first device may be configured to receive a first reply data packet, associated with the first inquiry, from a second device. The first reply data packet may comprise a second identification number associated with the second device. A first message may be transmitted to a data processing station. The first message may comprise the first identification number and the second identification number. The third device may be associated with a third identification number and may be configured to detect a second event. The third device may be configured to transmit a second inquiry in a second direction responsive to detecting the second event. The third device may be configured to receive a second reply data packet, associated with the second inquiry, from the second device. The second reply data packet may comprise the second identification number. The third device may be configured to transmit a second message to the data processing station. The second message may comprise the second identification number and the third identification number.

In an example, a first event may be detected. Responsive to detecting the first event, a first transceiver of a first device may be activated. Responsive to activating the first transceiver, a first inquiry may be transmitted, using the first transceiver, in a first direction. The first inquiry may be received by a second device via the first direction. The second device may comprise a second transceiver. Responsive to receiving the first inquiry, a first reply data packet may be transmitted, using the second transceiver, to the first device. The first reply data packet may comprise an identification number associated with the second device. A second event may be detected. Responsive to detecting the second event, a third transceiver of a third device may be activated. Responsive to activating the third transceiver, a second inquiry may be transmitted, using the third transceiver, in a second direction. The second inquiry may be received by the second device via the second direction. Responsive to receiving the second inquiry, a second reply data packet may be transmitted, using the second transceiver, to the third device. The second reply data packet may comprise the identification number associated with the second device.

DESCRIPTION OF THE DRAWINGS

While the techniques presented herein may be embodied in alternative forms, the particular embodiments illustrated in the drawings are only a few examples that are supplemental of the description provided herein. These embodiments are not to be interpreted in a limiting manner, such as limiting the claims appended hereto.

DETAILED DESCRIPTION

Subject matter will now be described more fully hereinafter with reference to the accompanying drawings, which form a part hereof, and which show, by way of illustration, specific example embodiments. This description is not intended as an extensive or detailed discussion of known concepts. Details that are known generally to those of ordinary skill in the relevant art may have been omitted, or may be handled in summary fashion.

The following subject matter may be embodied in a variety of different forms, such as methods, devices, components, and/or systems. Accordingly, this subject matter is not intended to be construed as limited to any example embodiments set forth herein. Rather, example embodiments are provided merely to be illustrative. Such embodiments may, for example, take the form of hardware, software, firmware or any combination thereof.

Figure 1:
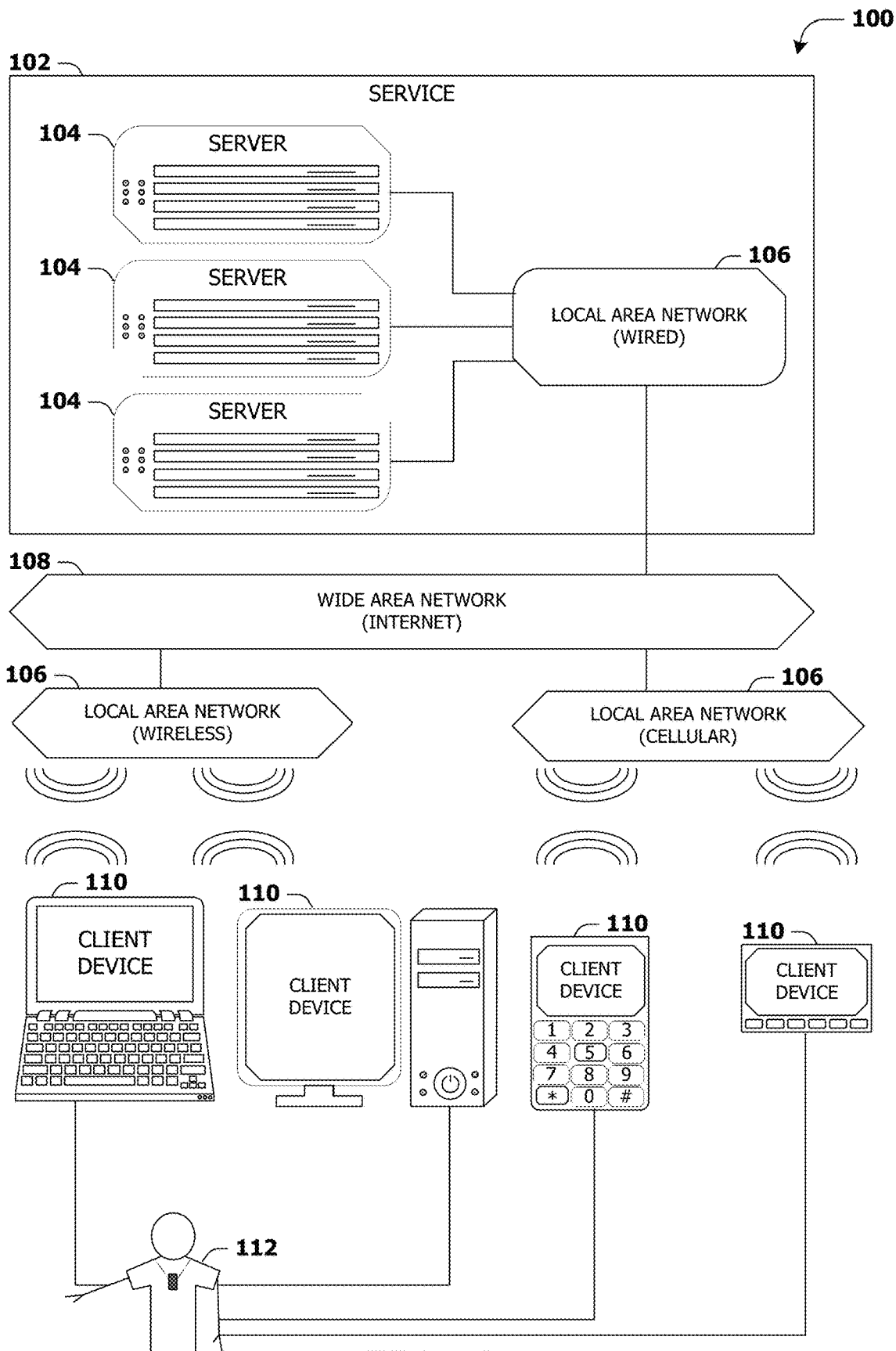
FIG. 1 is an illustration of a scenario involving various examples of networks that may connect servers and clients.

FIG. 1 is an interaction diagram of a scenario 100 illustrating a service 102 provided by a set of servers 104 to a set of client devices 110 via various types of networks. The servers 104 and/or client devices 110 may be capable of transmitting, receiving, processing, and/or storing many types of signals, such as in memory as physical memory states.

In the scenario 100 of FIG. 1, the service 102 may be accessed via a wide area network 108 (WAN) by a user 112 of one or more client devices 110, such as a portable media player (e.g., an electronic text reader, an audio device, or a portable gaming, exercise, or navigation device); a portable communication device (e.g., a camera, a phone, a wearable or a text chatting device); a workstation; and/or a laptop form factor computer. The respective client devices 110 may communicate with the service 102 via various connections to the wide area network 108.

One or more client devices 110 may comprise a cellular communicator and may communicate with the service 102 by connecting to the wide area network 108 via a wireless local area network 106 (LAN) provided by a cellular provider.

Alternatively and/or additionally, one or more client devices 110 may communicate with the service 102 by connecting to the wide area network 108 via a wireless local area network 106 provided by a location such as the user's home or workplace. The wireless local area network 106 may, for example, be a WiFi (Institute of Electrical and Electronics Engineers (IEEE) Standard 802.11) network or a Bluetooth (IEEE Standard 802.15.1) personal area network.

It may be appreciated that the servers 104 and the client devices 110 may communicate over various types of networks. Exemplary types of networks that may be accessed by the servers 104 and/or client devices 110 include mass storage, such as network attached storage (NAS), a storage area network (SAN), or other forms of computer or machine readable media.

The servers 104 of the service 102 may be interconnected directly, or through one or more other networking devices, such as routers, switches, and/or repeaters. The servers 104 may utilize a variety of physical networking protocols, such as Ethernet and/or Fiber Channel, and/or logical networking protocols, such as variants of an Internet Protocol (IP), a Transmission Control Protocol (TCP), and/or a User Datagram Protocol (UDP).

The servers 104 of the service 102 may be internally connected via a local area network 106. The local area network 106 may be organized according to one or more network architectures, such as server/client, peer-to-peer, and/or mesh architectures, and/or a variety of roles, such as administrative servers, authentication servers, security monitor servers, data stores for objects such as files and databases, business logic servers, time synchronization servers, and/or front-end servers providing a user-facing interface for the service 102.

The local area network 106 may be a wired network where network adapters on the respective servers 104 are interconnected via cables (e.g., coaxial and/or fiber optic cabling), and may be connected in various topologies (e.g., buses, token rings, meshes, and/or trees). The local area network 106 may include, e.g., analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art.

Alternatively and/or additionally, the local area network 106 may comprise one or more sub-networks, such as may employ differing architectures, may be compliant or compatible with differing protocols and/or may interoperate within the local area network 106. Additionally, a variety of local area networks 106 may be interconnected; e.g., a router may provide a link between otherwise separate and independent local area networks 106.

In the scenario 100 of FIG. 1, the local area network 106 of the service 102 is connected to a wide area network 108 that allows the service 102 to exchange data with other services 102 and/or client devices 110. The wide area network 108 may encompass various combinations of devices with varying levels of distribution and exposure, such as a public wide-area network (e.g., the Internet) and/or a private network (e.g., a virtual private network (VPN) of a distributed enterprise).

Figure 2:
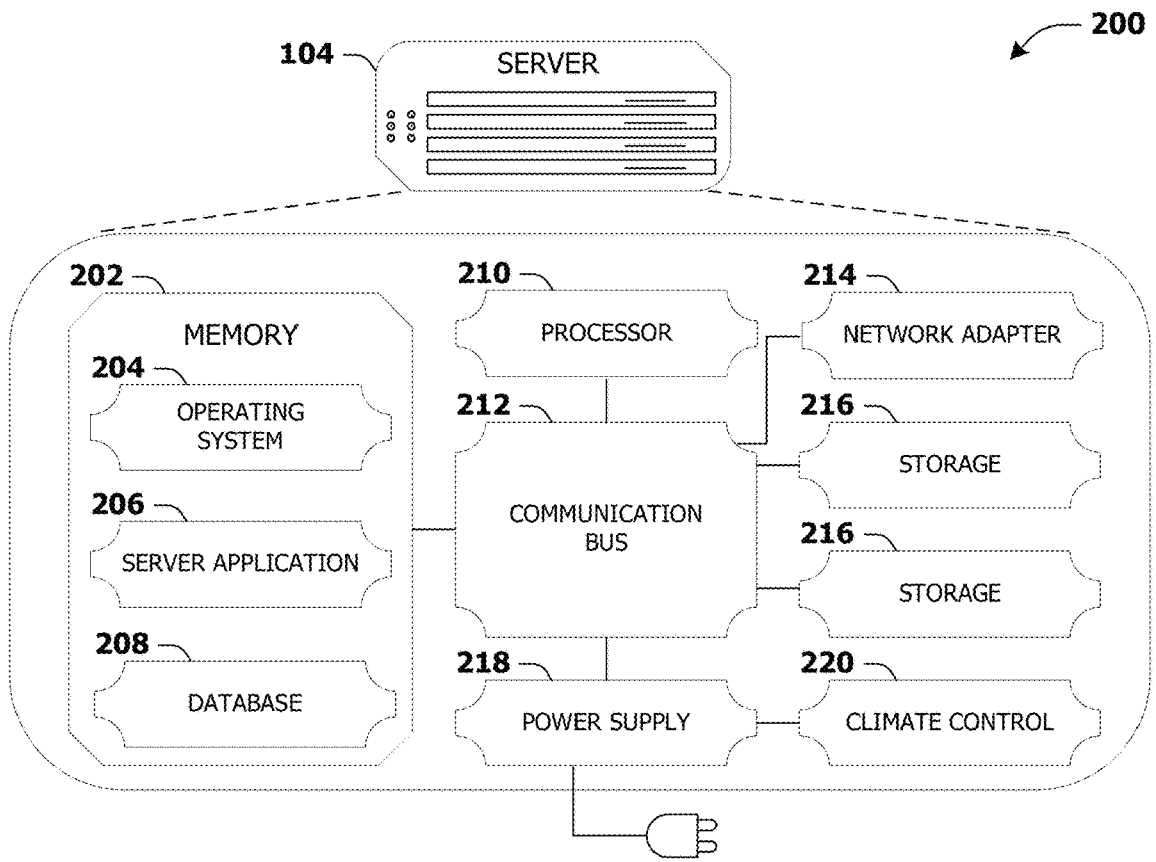
FIG. 2 is an illustration of a scenario involving an example configuration of a server that may utilize and/or implement at least a portion of the techniques presented herein.

FIG. 2 presents a schematic architecture diagram 200 of a server 104 that may utilize at least a portion of the techniques provided herein. Such a server 104 may vary widely in configuration or capabilities, alone or in conjunction with other servers, in order to provide a service such as the service 102.

The server 104 may comprise a variety of peripheral components, such as a wired and/or wireless network adapter 214 connectible to a local area network and/or wide area network; one or more storage components 216, such as a hard disk drive, a solid-state storage device (SSD), a flash memory device, and/or a magnetic and/or optical disk reader.

The server 104 may comprise memory 202 storing various forms of applications, such as an operating system 204; one or more server applications 206, such as a hypertext transport protocol (HTTP) server, a file transfer protocol (FTP) server, or a simple mail transport protocol (SMTP) server; and/or various forms of data, such as a database 208 or a file system.

The server 104 may comprise one or more processors 210 that process instructions. The one or more processors 210 may optionally include a plurality of cores; one or more coprocessors, such as a mathematics coprocessor or an integrated graphical processing unit (GPU); and/or one or more layers of local cache memory.

The server 104 may comprise a mainboard featuring one or more communication buses 212 that interconnect the processor 210, the memory 202, and various peripherals, using a variety of bus technologies, such as a variant of a serial or parallel AT Attachment (ATA) bus protocol; a Uniform Serial Bus (USB) protocol; and/or Small Computer System Interface (SCI) bus protocol. In a multibus scenario, a communication bus 212 may interconnect the server 104 with at least one other server.

The server 104 may operate in various physical enclosures, such as a desktop or tower, and/or may be integrated with a display as an "all-in-one" device. The server 104 may be mounted horizontally and/or in a cabinet or rack, and/or may simply comprise an interconnected set of components.

The server 104 may provide power to and/or receive power from another server and/or other devices. The server 104 may comprise a dedicated and/or shared power supply 218 that supplies and/or regulates power for the other components. The server 104 may comprise a shared and/or dedicated climate control unit 220 that regulates climate properties, such as temperature, humidity, and/or airflow.

The server 104 may include one or more other components that are not shown in the schematic diagram 200 of FIG. 2, such as a display; a display adapter, such as a graphical processing unit (GPU); input peripherals, such as a keyboard and/or mouse; and a flash memory device that may store a basic input/output system (BIOS) routine that facilitates booting the server 104 to a state of readiness. A plurality of such servers 104 may be configured and/or adapted to utilize at least a portion of the techniques presented herein.

Figure 3:
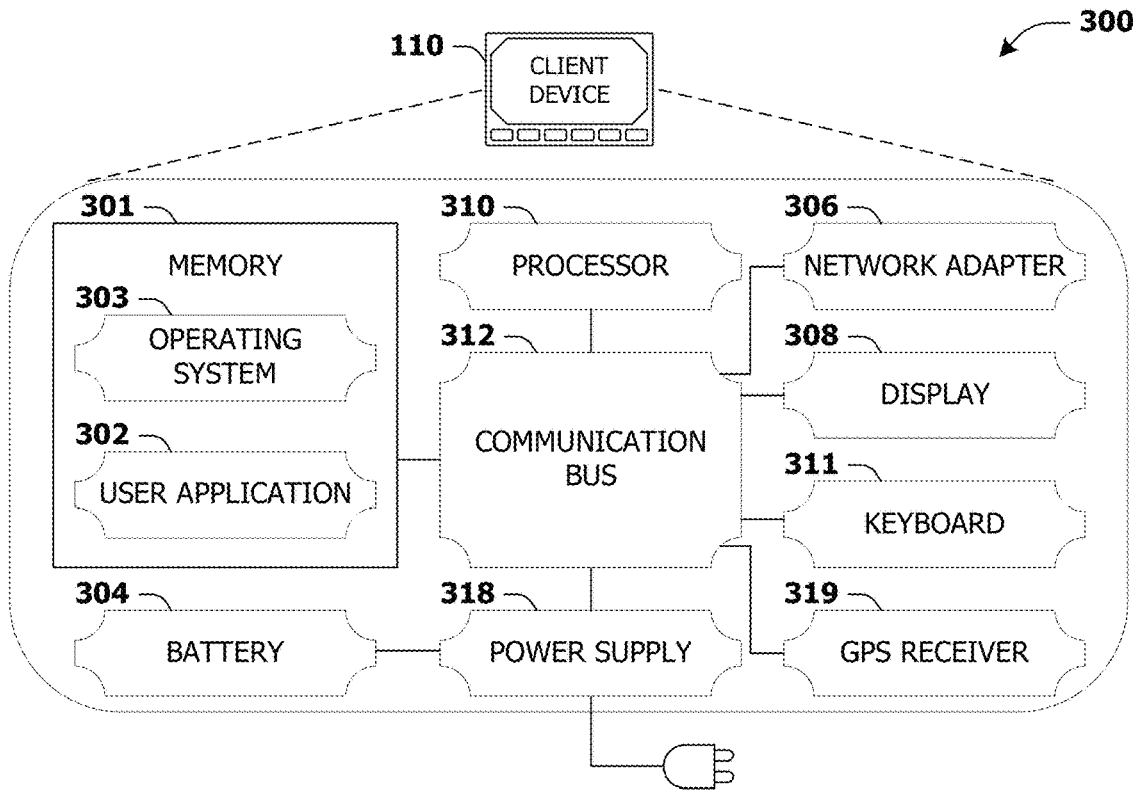
FIG. 3 is an illustration of a scenario involving an example configuration of a client that may utilize and/or implement at least a portion of the techniques presented herein.

FIG. 3 presents a schematic architecture diagram 300 of a client device 110 whereupon at least a portion of the techniques presented herein may be implemented. Such a client device 110 may vary widely in configuration or capabilities, in order to provide a variety of functionality to a user such as the user 112.

The client device 110 may comprise memory 301 storing various forms of applications, such as an operating system 303; one or more user applications 302, such as document applications, media applications, file and/or data access applications, communication applications such as web browsers and/or email clients, utilities, and/or games; and/or drivers for various peripherals.

In some examples, as a user 112 interacts with a software application on a client device 110 (e.g., an instant messenger and/or electronic mail application), descriptive content in the form of signals or stored physical states within memory (e.g., an email address, instant messenger identifier, phone number, postal address, message content, date, and/or time) may be identified.

In such examples, descriptive content may be stored, typically along with contextual content. For example, the source of an email address (e.g., a communication received from another user via an instant messenger application) may be stored as contextual content associated with the email address. Contextual content, therefore, may identify circumstances surrounding receipt of an email address (e.g., the date or time that the email address was received), and may be associated with descriptive content. Contextual content, may, for example, be used to subsequently search for associated descriptive content. For example, a search for email addresses received from specific individuals, received via an instant messenger application or at a given date or time, may be initiated.

The client device 110 may comprise one or more processors 310 that process instructions. The one or more processors 310 may optionally include a plurality of cores; one or more coprocessors, such as a mathematics coprocessor or an integrated graphical processing unit (GPU); and/or one or more layers of local cache memory.

The client device 110 may comprise a dedicated and/or shared power supply 318 that supplies and/or regulates power for other components, and/or a battery 304 that stores power for use while the client device 110 is not connected to a power source via the power supply 318. The client device 110 may provide power to and/or receive power from other client devices.

The client device 110 may comprise a variety of peripheral components, such as a wired and/or wireless network adapter 306 connectible to a local area network and/or wide area network; one or more output components, such as a display 308 coupled with a display adapter (optionally including a graphical processing unit (GPU)), a sound adapter coupled with a speaker, and/or a printer; input devices for receiving input from the user, such as a keyboard 311, a mouse, a microphone, a camera, and/or a touch-sensitive component of the display 308; and/or environmental sensors, such as a global positioning system (GPS) receiver 319 that detects the location, velocity, and/or acceleration of the client device 110, a compass, accelerometer, and/or gyroscope that detects a physical orientation of the client device 110.

The client device 110 may comprise a mainboard featuring one or more communication buses 312 that interconnect the processor 310, the memory 301, and various peripherals, using a variety of bus technologies, such as a variant of a serial or parallel AT Attachment (ATA) bus protocol; the Uniform Serial Bus (USB) protocol; and/or the Small Computer System Interface (SCI) bus protocol.

The client device 110 may include one or more other components that are not shown in the schematic architecture diagram 300 of FIG. 3, such as one or more storage components, such as a hard disk drive, a solid-state storage device (SSD), a flash memory device, and/or a magnetic and/or optical disk reader; and/or a flash memory device that may store a basic input/output system (BIOS) routine that facilitates booting the client device 110 to a state of readiness. In some examples, the client device 110 may include a climate control unit that regulates climate properties, such as temperature, humidity, and airflow.

The client device 110 may include one or more servers that may locally serve the client device 110 and/or other client devices of the user 112 and/or other individuals. For example, a locally installed webserver may provide web content in response to locally submitted web requests. Many such client devices 110 may be configured and/or adapted to utilize at least a portion of the techniques presented herein.

The client device 110 may serve the user in a variety of roles, such as a workstation, kiosk, media player, gaming device, and/or appliance. The client device 110 may therefore be provided in a variety of form factors, such as a desktop or tower workstation; an "all-in-one" device integrated with a display 308; a laptop, tablet, convertible tablet, or palmtop device; a wearable device mountable in a headset, eyeglass, earpiece, and/or wristwatch, and/or integrated with an article of clothing; and/or a component of a piece of furniture, such as a tabletop, and/or of another device, such as a vehicle or residence.

One or more computing devices and/or techniques are provided for determining a time-length of an action and/or determining compliance with a protocol based upon the time-length of the action. For example, a badge (e.g., an identification badge) may be assigned to an entity. The entity may be an employee of a healthcare facility and/or a company and/or the entity may be a device (e.g., equipment used by the healthcare facility and/or the company). In some examples, a protocol of the healthcare facility and/or the company may require that the entity enter a room (e.g., a washroom and/or a different type of room), interact with a dispense device (e.g., soap dispenser, sanitation liquid dispenser, water dispenser, etc.) and/or leave the room within a time-limit.

However, monitoring compliance (e.g., with the protocol) of the entity may require the use of significant resources including computer resources and/or human resources. To reduce the resources required to monitor compliance, the badge may comprise a first device used to communicate with one or more devices in the room using a wireless system (e.g., a radio frequency (RF) communication system, etc.). The first device and/or the one or more devices may be used to monitor compliance of the entity (e.g., with the protocol). The first device and/or the one or more devices may be used to determine a location (e.g., at a current time, at a previous time) of the entity. A report may be generated (e.g., and/or presented) based upon the compliance of the entity. Further, a location report may be generated (e.g., and/or presented). The location report may comprise a plurality of locations of the entity and/or a plurality of times corresponding to the plurality of locations.

Figure 4:
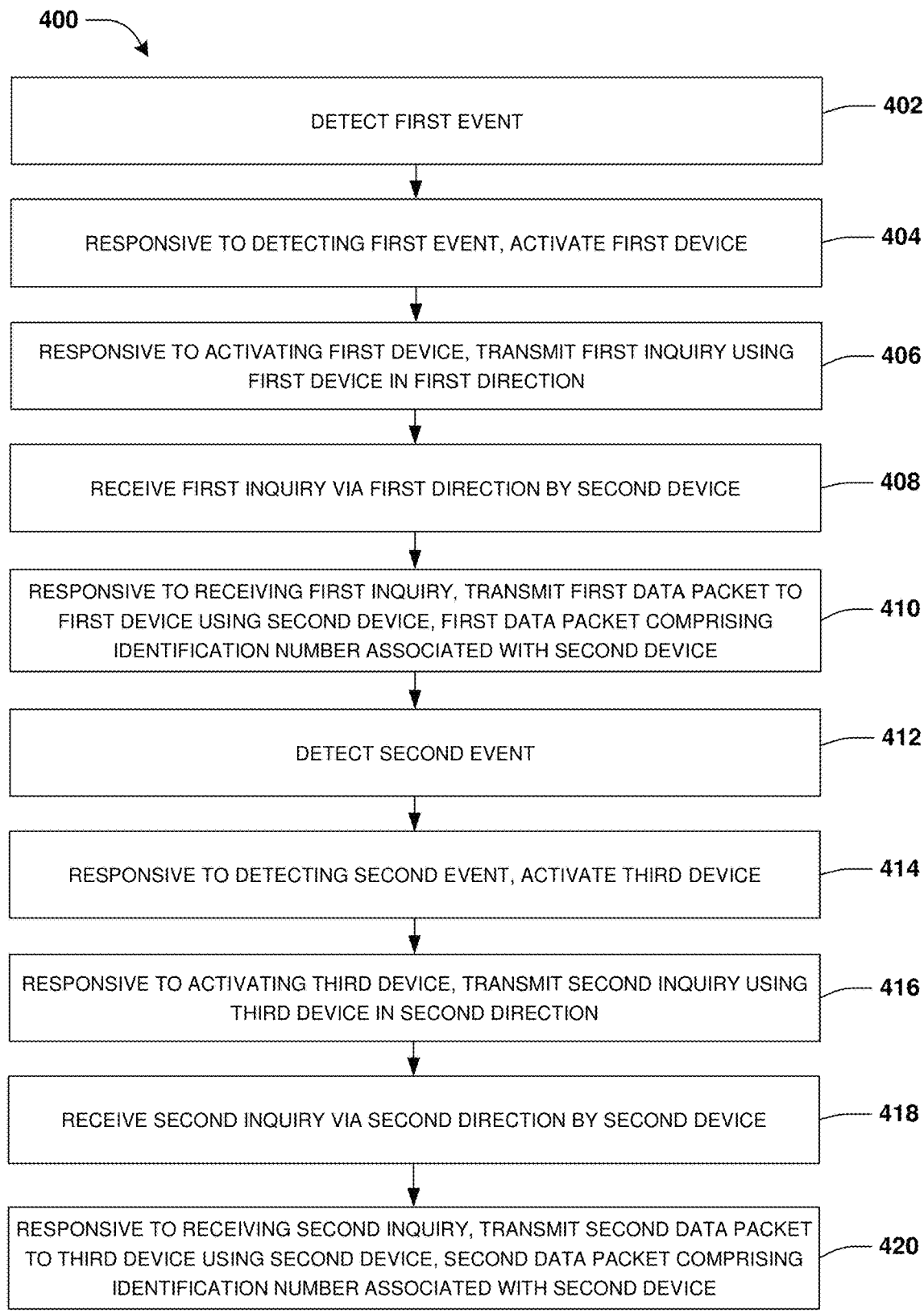
FIG. 4 is a flow chart illustrating an example method for determining a time-length of an action

An embodiment of determining a time-length of an action is illustrated by an example method 400 of FIG. 4. A wireless system (e.g., an RF system) may be configured for determining and/or monitoring compliance with one or more protocols (e.g., a health facility protocol, a hand-washing protocol, etc.) and/or monitoring a location of one or more entities. In some examples, the wireless system may comprise a first device. The first device may be associated with a first identification number. The first device may comprise a first event counter. For example, the first device may be coupled to a wall, a ceiling and/or an entrance of a room. A first infrared sensor may be comprised within the first device and/or may be coupled to the first device. The first infrared sensor may be configured to monitor a first location. The first location may comprise at least a portion of the room and/or at least a portion of the entrance. For example, the first infrared sensor may emit light through the first location and may sense motion (e.g., of one or more objects) at the first location.

At 402, a first event may be detected (e.g., by the first device). In some examples, the first event may be detected by receiving an indication of motion at the first location and/or by receiving an indication of a direction of motion at the first location from the first infrared sensor. The first device, the first infrared sensor and/or the first location may be positioned such that the indication of motion at the first location may be indicative of an entity entering a room. Alternatively and/or additionally, the first infrared sensor may comprise a set of (e.g., infrared) sensors configured to determine a direction of motion at the first location such that the indication of the direction of motion at the first location may be indicative of the entity entering the room.

In some examples, the entity may be a person who is an employee of a healthcare facility (e.g., a doctor, a nurse, a technician, etc.), a person who is an employee of a (e.g., different type of) facility and/or a company, a contractor, a patient of the healthcare facility, a customer of the company, etc. Alternatively and/or additionally, the entity may be an object (e.g., equipment, a device, etc.) that may be used at the healthcare facility, the facility and/or the company, etc. For example, the object may correspond to medical equipment (e.g., a medical device), machinery, a container (e.g., a container containing one or more of medical supplies, a substance, medicine, etc.) and/or a different type of object. In some examples, the medical equipment may comprise diagnostic equipment (e.g., medical imaging machines such as ultrasound machines, magnetic resonance imaging (MRI) machines, positron-emission tomography (PET) scanners, computed tomography (CT) scanners, and/or x-ray machines), treatment equipment (e.g., infusion pumps, medical lasers, and/or surgical machines), life support equipment (e.g., medical ventilators, incubators, anesthetic machines, heart-lung machines, and/or dialysis machines), medical monitors (e.g., monitors used to produce electrocardiograms (ECG), electroencephalograms (EEG), and/or blood pressure), medical laboratory equipment (e.g., equipment used to analyze blood, urine, genes and/or dissolved gasses), and/or therapeutic devices (e.g., physical therapy machines). A badge may be assigned to the entity that is configured to assist in tracking events and/or actions associated with the entity. In some examples, the badge may be a wearable (e.g., clip-on) device, a card-sized apparatus, a pin, glasses, a sticker, etc. Alternatively and/or additionally, the badge may be attached to the entity. In an example where the entity is a person, the badge may be worn by the person. In an example where the entity is the object, the badge may correspond to a device used to track the object and/or the badge may be attached to the object (e.g., the badge may be attached to the object using an adhesive).

At 404, responsive to detecting the first event, a first transceiver of a first device may be activated. The first transceiver may be a wireless system device. For example, the first transceiver may be a first RF module.

At 406, responsive to activating the first transceiver, a first inquiry may be transmitted by the first transceiver in a first direction. In some examples, the first inquiry may be a data packet. In some examples, the first direction may be based upon the first location and/or a position of the entity. In some examples, the first inquiry may be transmitted (e.g., in the first direction) using a first unidirectional antenna structure of the first device. Alternatively and/or additionally, the first unidirectional antenna structure may be circular polarized. Alternatively and/or additionally, the first device may receive and/or transmit data using half duplex (e.g., bidirectional) data flow.

It may be appreciated that using the first unidirectional antenna structure (rather than an omnidirectional antenna structure and/or a different type of antenna structure) may reduce multipath effects, may narrow reception of the first inquiry to within a selected area (e.g., the selected area may be based upon the first location) and/or may lead to greater efficiency/accuracy of the wireless system. In some examples, a beam width of the first unidirectional antenna may be less than or equal to 60 degrees. Alternatively and/or additionally, the beam width of the first unidirectional antenna may be greater than 60 degrees.

The wireless system may comprise a second device, which may comprise a second transceiver. The badge (e.g., assigned to the entity) may comprise the second device. The second transceiver may be a wireless system device. For example, the second transceiver may be a second RF module. In some examples, the badge may comprise an accelerometer and/or one or more capacitance sensors coupled to the second transceiver. The accelerometer may activate the second transceiver responsive to sensing movement of the badge and/or the accelerometer may deactivate the second transceiver responsive to sensing that the badge is not moving. For example, responsive to (e.g., the movement of) the entity (e.g., and/or the badge) entering the room, the second transceiver may be activated. Alternatively and/or additionally, the one or more capacitance sensors may activate the second transceiver responsive to sensing that the badge is attached to (e.g., worn by, held by, etc.) the entity and/or the one or more capacitance sensors may deactivate the second transceiver responsive to sensing that the badge is not attached to the entity.

At 408, the second device may receive the first inquiry via the first direction. In some examples, the first inquiry may be received (e.g., via the first direction) using a second unidirectional antenna structure of the second device. Alternatively and/or additionally, the second unidirectional antenna structure may be circular polarized. Alternatively and/or additionally, the second device may receive and/or transmit data using half duplex (e.g., bidirectional) data flow.

At 410, responsive to receiving the first inquiry, the second transceiver may transmit a first reply data packet to the first device. A reply data packet may be a data packet generated and/or transmitted in response to an inquiry. The first reply data packet may comprise a second identification number associated with the second device (e.g., and/or the badge). In some examples, the second device may be coupled to a first controller. The second identification number may be stored on the first controller. For example, the first controller may generate the first reply data packet comprising the second identification number. In some examples, the first reply data packet may be transmitted to the first device using the second unidirectional antenna structure.

In some examples, the second transceiver may transmit the first reply data packet to the first device responsive to a determination that a first signal strength of the first inquiry is greater than a first signal strength threshold. Alternatively and/or additionally, the first inquiry may be discarded responsive to a determination that the first signal strength of the first inquiry is less than the first signal strength threshold. For example, the first signal strength may be indicative of a distance between the first device and the second device (at the time the first inquiry is transmitted by the first transceiver). In some examples, the first signal strength threshold may be configured such that the first signal strength is greater than the first signal strength threshold if the entity and/or the badge are within a first threshold distance from the first device. The first threshold distance may correspond to a maximum distance, between the first device and the second device, required for the entity to be entering the room.

In some examples, responsive to determining that the first event is associated with the entity entering the room, the second device may be paired with the first device. For example, responsive to determining that the direction of motion at the first location is indicative of the entity entering the room, the first device and the second device may exchange pairing information (e.g., comprised within the first inquiry, the first reply data packet and/or other data packets exchanged between the first device and the second device). Alternatively and/or additionally, responsive to determining that the direction of motion at the first location is indicative of the entity leaving the room at a time when the second device is not paired with the first device, the first reply data packet may be discarded.

In some examples, the first reply data packet may comprise a first counter value. For example, a counter may be coupled to the second device and/or comprised within the second device. The counter may be configured to increment a counter value (e.g., by one) periodically. The counter may be configured to increment the counter value based upon a time interval between increments associated with the counter. The counter value may be equal to the first counter value at a first time that the second transceiver transmits the first reply data packet. Alternatively and/or additionally, the first reply data packet may not comprise the first counter value and/or the counter may not be coupled to the second device and/or comprised within the second device.

Alternatively and/or additionally, the first reply data packet may comprise a first received signal strength indicator (RSSI) comprising an indication of the first signal strength (associated with the first inquiry).

The wireless system may comprise a third device. The third device may comprise a second event counter. For example, the third device may be coupled to a dispense device (e.g., soap dispenser, sanitation liquid dispenser, water dispenser, etc.) and/or may be comprised within the dispense device. A second infrared sensor may be comprised within the third device and/or may be coupled to the third device. The second infrared sensor may be configured to monitor a second location. The second location may comprise an area of the room adjacent to (e.g., below, above, in front of, etc.) the dispense device and/or the third device. For example, the second infrared sensor may emit light through the second location and may sense motion (e.g., of one or more objects) at the second location.

At 412, a second event may be detected (e.g., by the third device). In some examples, the second event may be detected by receiving an indication of motion at the second location from the second infrared sensor. The third device, the second infrared sensor and/or the second location may be positioned such that the indication of motion at the second location may be indicative of the entity interacting with the dispense device.

At 414, responsive to detecting the second event, a third transceiver of the third device may be activated. The third transceiver may be a wireless system device. For example, the third transceiver may be a third RF module.

At 416, responsive to activating the third transceiver, a second inquiry may be transmitted by the third transceiver in a second direction. In some examples, the second inquiry may be a data packet. In some examples, the second direction may be based upon the second location and/or a position of the entity. In some examples, the second inquiry may be transmitted (e.g., in the second direction) using a third unidirectional antenna structure of the third device. Alternatively and/or additionally, the third unidirectional antenna may be circular polarized. Alternatively and/or additionally, the third device may receive and/or transmit data using half duplex (e.g., bidirectional) data flow.

At 418, the second device (e.g., comprised within the badge assigned to the entity) may receive the second inquiry via the second direction. In some examples, the second inquiry may be received (e.g., via the second direction) using the second unidirectional antenna structure. Alternatively and/or additionally, the second device may comprise a fourth unidirectional antenna structure. For example, the second inquiry may be received using the fourth unidirectional antenna structure. In some examples, the second unidirectional antenna structure and/or the fourth unidirectional antenna structure may be coupled to a first antenna switch.

The second unidirectional antenna structure may be positioned at a first angle with respect to the badge and the fourth unidirectional antenna structure may be positioned at a second angle with respect to the badge. For example, the second unidirectional antenna structure may be positioned vertically (e.g., such that the fourth unidirectional antenna structure faces the ceiling, faces the first transceiver, faces the first device, faces other event counters positioned above the entity, etc.). Alternatively and/or additionally, the fourth unidirectional antenna structure may be positioned horizontally (e.g., such that the fourth unidirectional antenna structure faces the wall, faces the dispense device, faces the third device, faces other event counters positioned within and/or near dispense devices). In some examples, a direction that the second unidirectional antenna structure faces may be orthogonal to a direction that the fourth unidirectional antenna structure faces. Alternatively and/or additionally, an angle between the direction that the second unidirectional antenna structure faces and the direction that the fourth unidirectional antenna structure faces may be less than or greater than 90 degrees.

In some examples, the first antenna switch, the first controller and/or the second transceiver may be configured to transmit data packets using the second unidirectional antenna structure responsive to receiving inquiries using the second unidirectional antenna structure. For example, responsive to receiving the first inquiry, using the second unidirectional antenna structure, the first reply data packet may be transmitted to the first device, using the second unidirectional antenna structure. Alternatively and/or additionally, the first antenna switch, the first controller and/or the second transceiver may be configured to transmit data packets to wireless devices using the fourth unidirectional antenna structure responsive to receiving inquiries using the fourth unidirectional antenna structure. For example, responsive to receiving the second inquiry, using the fourth unidirectional antenna structure, the second reply data packet may be transmitted to the third device, using the fourth unidirectional antenna structure.

At 420, responsive to receiving the second inquiry, the second transceiver may transmit a second reply data packet to the third device. The second reply data packet may comprise the second identification number associated with the second device (e.g., and/or the badge). The second reply data packet may comprise a second counter value corresponding to a second time that the second transceiver transmits the second reply data packet. Alternatively and/or additionally, the second reply data packet may not comprise the second counter value.

In some examples, the second transceiver may transmit the second reply data packet to the third device responsive to a determination that a second signal strength of the second inquiry is greater than a second signal strength threshold. Alternatively and/or additionally, the second inquiry may be discarded responsive to a determination that the second signal strength of the second inquiry is less than the second signal strength threshold. For example, the second signal strength may be indicative of a distance between the third device and the second device (at the time the second inquiry is transmitted by the third transceiver). In some examples, the second signal strength threshold may be configured such that the second signal strength is greater than the second signal strength threshold if the entity and/or the badge are within a second threshold distance from the third device and/or the third transceiver. The second threshold distance may correspond to a maximum distance, between the second device and the third device, required for the entity to be interacting with the dispense device.

Alternatively and/or additionally, the second reply data packet may comprise a second RSSI comprising an indication of the second signal strength (associated with the second inquiry).

In some examples, the first device may detect a third event by receiving an indication of motion and/or an indication of a direction of motion at the first location. For example, the set of sensors of the first infrared sensor may determine a second direction of motion at the first location indicative of the entity exiting the room. Alternatively and/or additionally, the first device may comprise a third infrared sensor and/or may be coupled to the third infrared sensor configured to monitor a third location. Alternatively and/or additionally, the third infrared sensor may be comprised within a third event counter and/or may be coupled to the third event counter. The third event counter may be coupled to a wall, a ceiling and/or the entrance. The third location may comprise at least a portion of the entrance and/or outside of the room (e.g., a hallway). For example, the third infrared sensor may emit light through the third location and may sense motion (e.g., of one or more objects) at the third location.

In some examples, responsive to detecting the third event, the first transceiver (e.g., or a fourth device coupled to the third event counter) may be activated. Responsive to activating the first transceiver (e.g., or the fourth device), a third inquiry may be transmitted in the first direction (e.g., or a third direction). In some examples, the third inquiry may be a data packet. The second device (e.g., comprised within the badge assigned to the entity) may receive the third inquiry via the first direction (e.g., or the third direction). Responsive to receiving the third inquiry, the second transceiver may transmit a third reply data packet to the first device (e.g., or the fourth device). The third reply data packet may comprise the second identification number associated with the second device (e.g., and/or the badge). The third reply data packet may comprise a third counter value corresponding to a third time that the second transceiver transmits the third reply data packet. Alternatively and/or additionally, the third reply data packet may not comprise the third counter value.

In some examples, responsive to determining that the third event is associated with the entity exiting the room, the second device may be unpaired with the first device. Alternatively and/or additionally, responsive to determining that the second direction of motion is indicative of the entity exiting the room at a time when the second device is not paired with the first device, the third reply data packet may be discarded.

In some examples, the first device may generate a first message based upon the first reply data packet. In some examples, the first message may be generated based upon a determination that the direction of motion at the first location is indicative of the entity entering the room. The first message may comprise the second identification number associated with the second device (e.g., and/or the badge), a first time value, the first identification number associated with the first device, an indication of the direction of motion at the first location (indicative of the entity entering the room) and/or an indication that the first device and the second device are paired (e.g., pairing status). For example, the first identification number may be stored on a second controller coupled to the first device. The first transceiver may transmit the first message to a data collection device and/or a data processing station using a first omnidirectional antenna structure of the first device. Alternatively and/or additionally, the first transceiver may transmit the first message to one or more first repeater devices. In some examples, the first omnidirectional antenna structure may have a 360 degree transmit pattern. Alternatively and/or additionally, the first omnidirectional antenna structure may have vertical polarization.

In some examples, the first device may generate (and/or transmit) the first message responsive to a determination that a third signal strength of the first reply data packet is greater than a third signal strength threshold. Alternatively and/or additionally, the first reply data packet may be discarded responsive to a determination that the third signal strength of the first reply data packet is less than the third signal strength threshold. For example, the third signal strength may be indicative of a distance between the first device and the second device (at the time the first reply data packet is transmitted by the second transceiver). In some examples, the third signal strength is greater than the third signal strength threshold if the entity and/or the badge are within a third threshold distance from the first device and/or the first transceiver. The third threshold distance may correspond to a maximum distance, between the first device and the second device, required for the entity to be entering the room.

Alternatively and/or additionally, the first device may determine the first signal strength of the first inquiry received by the second transceiver based upon the first RSSI. The first device may generate (and/or transmit) the first message responsive to a determination that the first RSSI is greater than a first RSSI threshold.

In some examples, where the first reply data packet comprises the first counter value and the second device comprises the counter, the first time value may comprise an indication of the first counter value. Alternatively and/or additionally, where the first reply data packet does not comprise the first counter value and/or the second device does not comprise the counter, the first time value may be generated by the first device (e.g., such that the first time value is generated based upon a value that is not stored in the first reply data packet and/or is not generated based upon a value stored in the first reply data packet). For example, the first time value may be indicative of the first time that the first reply data packet was received by the first device. For example, the first time value may be generated using a first timing device of the first device, such as a second counter of the first device and/or a first clock (e.g., a real time clock and/or a digital clock) of the first device.

Alternatively and/or additionally, the first message may not comprise the first time value (e.g., the second device may not comprise the counter and/or the first device may not comprise the first timing device). For example, responsive to receiving the first message by the one or more first repeater devices and/or by the data collection device, a first timestamp may be assigned to the first message (by the one or more repeater devices and/or by the data collection device).

Alternatively and/or additionally, the third device may generate a second message based upon the second reply data packet. The second message may comprise the second identification number, a second time value, a third identification number associated with the third device and/or an indication of the entity interacting with the dispense device. For example, the third identification number may be stored on a third controller coupled to the third device. The third transceiver may transmit the second message to the data collection device and/or the data processing station using a second omnidirectional antenna structure of the first device. Alternatively and/or additionally, the third transceiver may transmit the second message to one or more second repeater devices.

In some examples, the third device may generate (and/or transmit) the second message responsive to a determination that a fourth signal strength of the second reply data packet is greater than a fourth signal strength threshold. Alternatively and/or additionally, the second reply data packet may be discarded responsive to a determination that the fourth signal strength of the second reply data packet is less than the fourth signal strength threshold. For example, the fourth signal strength may be indicative of a distance between the third device and the second device (at the time the second reply data packet is transmitted by the second transceiver). In some examples, the fourth signal strength is greater than the fourth signal strength threshold if the entity and/or the badge are within a fourth threshold distance from the third device. The fourth threshold distance may correspond to a maximum distance, between the third device and the second device, required for the entity to be interacting with the dispense device.

Alternatively and/or additionally, the third device may determine the second signal strength of the first inquiry received by the second transceiver based upon the second RSSI. The third device may generate (and/or transmit) the second message responsive to a determination that the second RSSI is greater than a second RSSI threshold.

In some examples, where the second reply data packet comprises the second counter value and the second device comprises the counter, the second time value may comprise an indication of the second counter value. Alternatively and/or additionally, where the second reply data packet does not comprise the second counter value and/or the second device does not comprise the counter, the second time value may be generated by the third device (e.g., such that the second time value is generated based upon a value that is not stored in the second reply data packet and/or is not generated based upon a value stored in the second reply data packet).

For example, the second time value may be indicative of the second time that the second reply data packet was received by the third device. For example, the second time value may be generated using a second timing device of the third device, such as a third counter of the third device and/or a second clock (e.g., a real time clock and/or a digital clock) of the third device. In some examples, the first timing device (of the first device) and the second timing device (of the third device) and/or other timing devices associated with the wireless system may (automatically) be synchronized periodically (e.g., once per day, once per week, etc.). Alternatively and/or additionally, the first timing device and the second timing device and/or the other timing devices may be synchronized manually (e.g., during maintenance visits, by an administrator, etc.).

Alternatively and/or additionally, the second message may not comprise the second time value (e.g., the second device may not comprise the counter and/or the third device may not comprise the second timing device). For example, responsive to receiving the second message by the one or more second repeater devices and/or by the data collection device, a second timestamp may be assigned to the second message (by the one or more second repeater devices and/or by the data collection device).

Alternatively and/or additionally, the first device (e.g., or the third event counter) may generate a third message based upon the third reply data packet. The third message may comprise the second identification number, a third time value, the first identification number associated with the first device (or a fourth identification number associated with the fourth device), an indication of the second direction of motion at the first location (indicative of the entity exiting the room) and/or an indication that the first device and the second device are unpaired (e.g., pairing status). The third message may be transmitted to the data collection device and/or the data processing station using the second omnidirectional antenna structure (e.g., or a third omnidirectional antenna structure of the fourth device). Alternatively and/or additionally, the third message may be transmitted to one or more third repeater devices.

In some examples, where the third reply data packet comprises the third counter value and the second device comprises the counter, the third time value may comprise an indication of the third counter value. Alternatively and/or additionally, the third time value may be generated by the first device (e.g., or the third event counter) (e.g., such that the third time value is generated based upon a value that is not stored in the third reply data packet and/or is not generated based upon a value stored in the third reply data packet). For example, the third time value may be indicative of the third time that the third reply data packet was received by the first device (e.g., or the fourth device). Alternatively and/or additionally, the third message may not comprise the third time value. For example, responsive to receiving the third message by the one or more third repeater devices and/or by the data collection device, a third timestamp may be assigned to the third message (by the one or more third repeater devices and/or by the data collection device).

In some examples, the first transceiver may periodically transmit the first message to the data collection device and/or the data processing station (e.g., in order to ensure reception of the first message by the data collection device and/or the data processing station). A first number of transmissions of the first message may be configured based upon a success rate of transmissions of the first transceiver. Alternatively and/or additionally, the first transceiver may periodically transmit the first message to the data collection device and/or the data processing station until a confirmation message (e.g., confirming receipt of the first message) is received from the data collection device and/or the data processing station. Alternatively and/or additionally, the first transceiver may transmit the first message by using a listen before talk (LBT) system.

The third transceiver may periodically transmit the second message to the data collection device and/or the data processing station (e.g., in order to ensure reception of the second message by the data collection device and/or the data processing station). A second number of transmissions of the second message may be configured based upon a success rate of transmissions of the third transceiver. Alternatively and/or additionally, the third transceiver may periodically transmit the second message to the data collection device and/or the data processing station until a confirmation message (e.g., confirming receipt of the third message) is received from the data collection device and/or the data processing station. Alternatively and/or additionally, the third transceiver may transmit the second message by using the LBT system.

The first transceiver (e.g., or the fourth device) may periodically transmit the third message to the data collection device and/or the data processing station (e.g., in order to ensure reception of the third message by the data collection device and/or the data processing station). A third number of transmissions of the third message may be configured based upon a success rate of transmissions of the first transceiver (e.g., or the fourth device). Alternatively and/or additionally, the first transceiver (e.g., or the fourth device) may periodically transmit the third message to the data collection device and/or the data processing station until a confirmation message (e.g., confirming receipt of the third message) is received from the data collection device and/or the data processing station. Alternatively and/or additionally, the first transceiver (e.g., or the fourth device) may transmit the third message by using the LBT system.

In some examples, the first transceiver may transmit the first message to the data collection device, the third transceiver may transmit the second message to the data collection device and/or the first transceiver (e.g., or the fourth device) may transmit the third message to the data collection device. In some examples, the data collection device may be configured to transmit the first message, the second message and/or the third message to the data processing station. Alternatively and/or additionally, the first transceiver may transmit the first message (e.g., directly) to the data processing station, the third transceiver may transmit the second message (e.g., directly) to the data processing station and/or the first transceiver (e.g., or the fourth device) may transmit the third message (e.g., directly) to the data processing station.

A time-length of an action may be generated (e.g., by the data processing station) based upon an evaluation of the first message and the second message. The action may comprise the entity entering the room and interacting with the dispense device. In some examples, the data processing station may identify the entity based upon the second identification number within the first message, the second message and/or the third message. Alternatively and/or additionally, the data processing station may identify the first event based upon the first message. For example, the data processing station may identify the first event (e.g., the entity entering the room) based upon the indication of the direction of motion at the first location (comprised within the first message). Alternatively and/or additionally, the data processing station may identify the first event based upon the indication that the first device and the second device are paired. Alternatively and/or additionally, the data processing station may determine that the first device and the second device are paired based upon the indication of the direction of motion at the first location (comprised within the first message). Alternatively and/or additionally, the data processing station may identify the second event based upon the second message.

An operation (e.g., a mathematical operation) may be performed on the first time value corresponding to the first event (e.g., and/or the first timestamp) and the second time value corresponding to the second event (e.g., and/or the second timestamp) to determine the time-length of the action. The time-length of the action may correspond to a time between transmission of the first reply data packet (e.g., by the second transceiver) and transmission of the second reply data packet (e.g., by the second transceiver) during which the entity may enter the room and interact with the dispense device.

In some examples, the first message may not comprise the first time value and/or the first timestamp may not be assigned to the first message. Alternatively and/or additionally, the second message may not comprise the second time value and/or the second timestamp may not be assigned to the second message. In some examples, the data processing station may determine the time-length of the action by determining a time-length between receiving the first message and receiving the second message. For example, responsive to receiving the first message, the data processing station may activate a timer. Responsive to receiving the second message, the data processing station may determine the time-length of the action based upon a timing value of the timer. Alternatively and/or additionally, the data processing station may determine a first time of reception of the first message and a second time of reception of the second message. An operation (e.g., a mathematical operation) on the first time of reception of the first message and/or the second time of reception of the second message may be performed to determine the time-length of the action.

In some examples, the healthcare facility (e.g., and/or the company) may have a protocol for entering the room and interacting with the dispense device. For example, the protocol may require a time-limit between entering the room and interacting with the dispense device. In some examples, the data processing station may determine compliance with the protocol by comparing the time-length of the action with the time-limit. In an example, the time-length of the action may be 13 seconds and the time-limit associated with the protocol may be 15 seconds. Accordingly, the data processing station may determine that the time-length of the action is compliant with the protocol. In a second example, the time-length of the action may be 17 seconds and the time-limit associated with the protocol may be 15 seconds. Accordingly, the data processing station may determine that the time-length of the action is not compliant with the protocol. In some examples, a report may be generated (e.g., by the data processing station) comprising the second identification number, the time-length of the action and/or the compliance with the protocol.

In some examples, a time-length of a second action may be generated based upon an evaluation of the first message and the third message. The second action may comprise the entity entering the room, interacting with the dispense device and exiting the room. Alternatively and/or additionally, the second action may comprise the entity entering the room and exiting the room. An operation (e.g., a mathematical operation) may be performed on the first time value corresponding to the first event (e.g., and/or the first time- stamp) and the third time value corresponding to the third event (e.g., and/or the third timestamp) to determine the time-length of the second action. For example, the data processing station may identify the third event (e.g., the entity exiting the room) based upon the indication of the second direction of motion at the first location (comprised within the third message). Alternatively and/or additionally, the data processing station may determine that the first device and the second device are unpaired based upon the indication of the second direction of motion at the first location (comprised within the third message). The time-length of the second action may correspond to a time between transmission of the first reply data packet (e.g., by the second transceiver) and transmission of the third reply data packet (e.g., by the second transceiver) during which the entity may enter the room, interact with the dispense device and exit the room (and/or the entity may enter the room and exit the room, without interacting with the dispense device).

In some examples, the healthcare facility (e.g., and/or the company) may have a second protocol for entering the room, interacting with the dispense device and exiting the room. For example, the second protocol may require a second time-limit between entering the room, interacting with the dispense device and exiting the room. In some examples, the data processing station may determine compliance with the second protocol by comparing the time-length of the second action with the second time-limit. In some examples, the report may be generated (e.g., by the data processing station) comprising the second identification number, the time-length of the second action and/or the compliance with the second protocol.

Alternatively and/or additionally, the healthcare facility (e.g., and/or the company) may have a third protocol for entering the room and exiting the room. For example, the third protocol may require a third time-limit between entering the room and exiting the room. In some examples, the data processing station may determine compliance with the third protocol by comparing the time-length of the second action with the third time-limit. In some examples, the report may be generated (e.g., by the data processing station) comprising the second identification number, the time-length of the second action and/or the compliance with the third protocol.

In some examples, the first transceiver, the second transceiver, the third transceiver and/or the fourth device may communicate (e.g., perform transmissions of data and/or receptions of data) using the wireless system (e.g., the RF system). In some examples, the first transceiver may transmit the first inquiry using an ultra-high frequency (UHF) band (e.g., and/or a different band), the second transceiver may transmit the first reply data packet, the second reply data packet and/or the third reply data packet using the UHF band (e.g., and/or a different band), the third transceiver may transmit the second inquiry using the UHF band (e.g., and/or a different band) and/or the first transceiver (e.g., or the fourth device) may transmit the third inquiry using the UHF band (e.g., and/or a different band). In some examples, the first transceiver may transmit the first message (e.g., to the data collection device and/or the data processing station) using the UHF band (e.g., and/or a different band), the third transceiver may transmit the second message using the UHF band (e.g., and/or a different band) and/or the first transceiver (e.g., or the fourth device) may transmit the third message using the UHF band (e.g., and/or a different band).

In some examples, a location (e.g., at a current time and/or a previous time) of the entity (e.g., a person and/or an object)

may be determined by the data processing station based upon a plurality of data packets and/or a plurality of messages associated with the entity. For example, the data processing station may determine that an event counter received a data packet from the second device at a given time. In some examples, the location of the entity at the given time may be determined based upon an identification number of the event counter comprised within a message (e.g., transmitted to the data processing station) generated based upon the data packet. Alternatively and/or additionally, the data processing station may determine the location of the entity at the given time based upon a pairing status of the second device at the given time.

In some examples, the location of the entity may be determined, monitored and/or tracked (by the data processing station). In an example where the entity is an object, the location of the entity may be determined, monitored and/or tracked in association with physical asset tracking. Alternatively and/or additionally, the location of the entity may be compared with one or more restricted locations. The one or more restricted locations may correspond to one or more of outside of the facility, a room that the entity is unauthorized to enter and/or be in, etc. In an example, the entity may correspond to a person and/or a restricted location of the one or more restricted locations may correspond to an area that the person is unauthorized to enter and/or be in. In an example, the entity may correspond to a device that is sensitive to moisture and/or a restricted location of the one or more restricted locations may correspond to a room having a high level of moisture. In an example, the entity may correspond to a device that is limited to performing operations within the facility and/or a restricted location of the one or more restricted locations may correspond to outside of the facility. In some examples, the location of the entity may be monitored and/or compared with the one or more restricted locations periodically (e.g., every minute, every hour, etc.). Responsive to determining that the entity is within a restricted location of the one or more restricted locations, a notification indicative of the entity being at the restricted location may be transmitted to an exemplary device (e.g., the exemplary device may be associated with a user, such as an employee and/or an administrator, associated with the facility).

In some examples, a location report may be generated (e.g., and/or presented). The location report may comprise a plurality of locations of the entity and/or a plurality of times corresponding to the plurality of locations. In an example, the location report may be indicative of a first exemplary location (e.g., a first exemplary room, such as room 106 of the facility), a first exemplary time associated with the first exemplary location (e.g., the first exemplary time may correspond to a period of time during which the entity is at the first exemplary location), a second exemplary location (e.g., a second exemplary room, such as room 110 of the facility), a second exemplary time associated with the second exemplary location (e.g., the second exemplary time may correspond to a period of time during which the entity is at the second exemplary location), etc.

In some examples, the location of the entity may be more accurately determined when the data processing station has access to time values (e.g., the first time value, the second time value, etc.), timestamps (e.g., the first timestamp, the second timestamp, etc.), and/or times of reception (e.g., the first time of reception, the second time of reception, etc.). For example, a threshold level of RF interference and/or a threshold level of RF activity surrounding the first device, the third device, one or more repeater devices, the data collection device and/or the data processing station may inhibit data packets and/or messages (e.g., the first reply data packet, the second reply data packet, the first inquiry, the second inquiry, the first message, the second message, etc.) from being received and/or processed.

For example, due to RF interference and/or RF activity, the data processing station may determine that an exemplary badge entered an exemplary room, and shortly afterwards, the data processing station may determine that the exemplary badge interacted with an exemplary dispense device in a second exemplary room (without determining that the exemplary badge has exited the exemplary room and/or that the exemplary badge has entered the second exemplary room). In some examples, a location of the exemplary badge (e.g., and/or a location of an exemplary entity associated with the exemplary badge) cannot be determined (e.g., without access to time values, timestamps, times of reception, etc.) until it is determined that the exemplary badge has exited the exemplary room or the second exemplary room.

In some examples, responsive to determining that RF interference is greater than the threshold level of RF interference and/or that RF activity is greater than the threshold level of RF activity, the first device, the third device, one or more repeater devices, the data collection device and/or the data processing station may generate counter values, time values, timestamps and/or times of reception for data packets and/or messages that are transmitted and/or received, which may be used to determine the location of the exemplary badge.

Figure 5A:
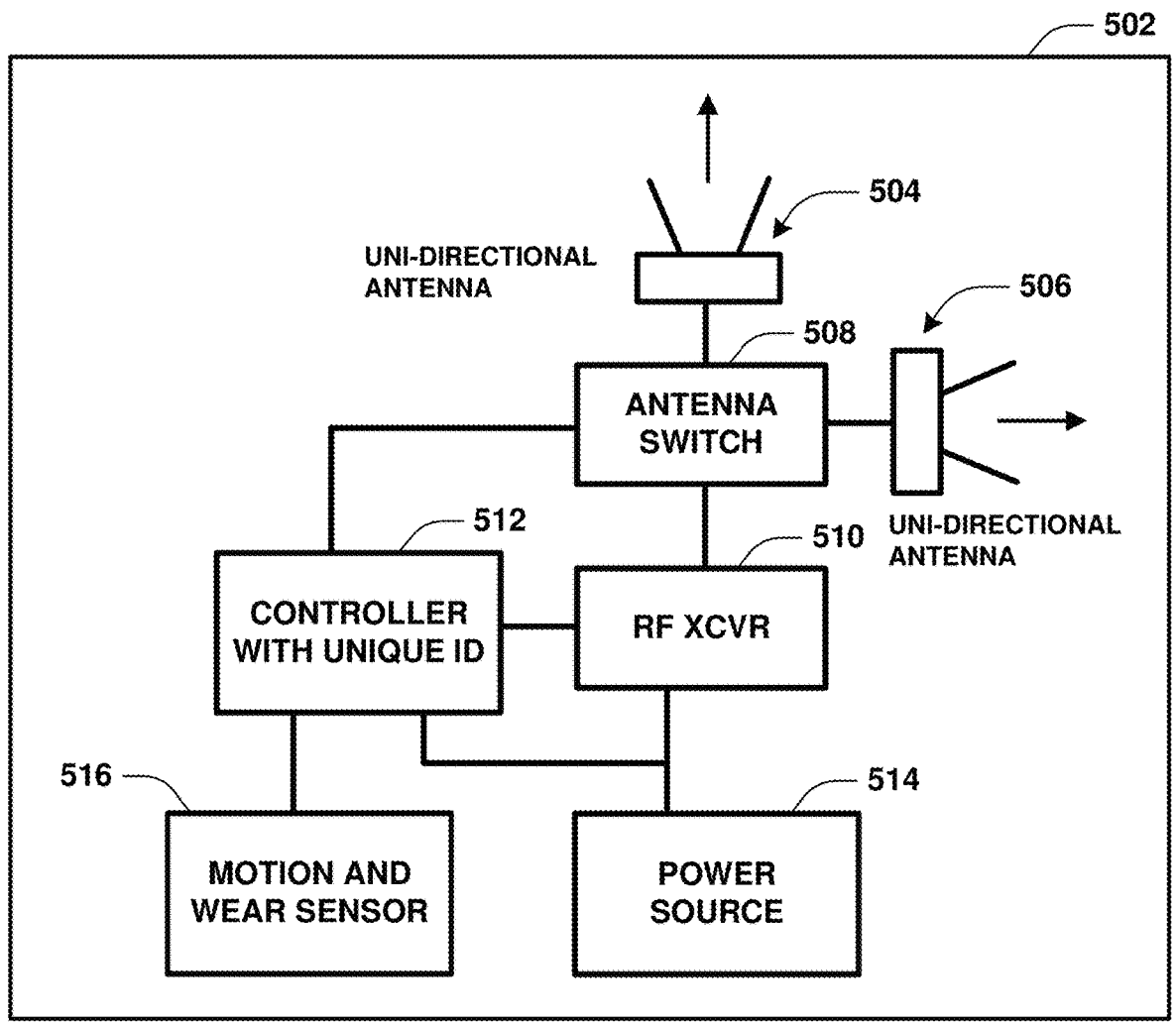
FIG. 5A is a component block diagram illustrating an example of a first component, of a wireless system, configured for assisting in tracking one or more entities.
Figure 5B:
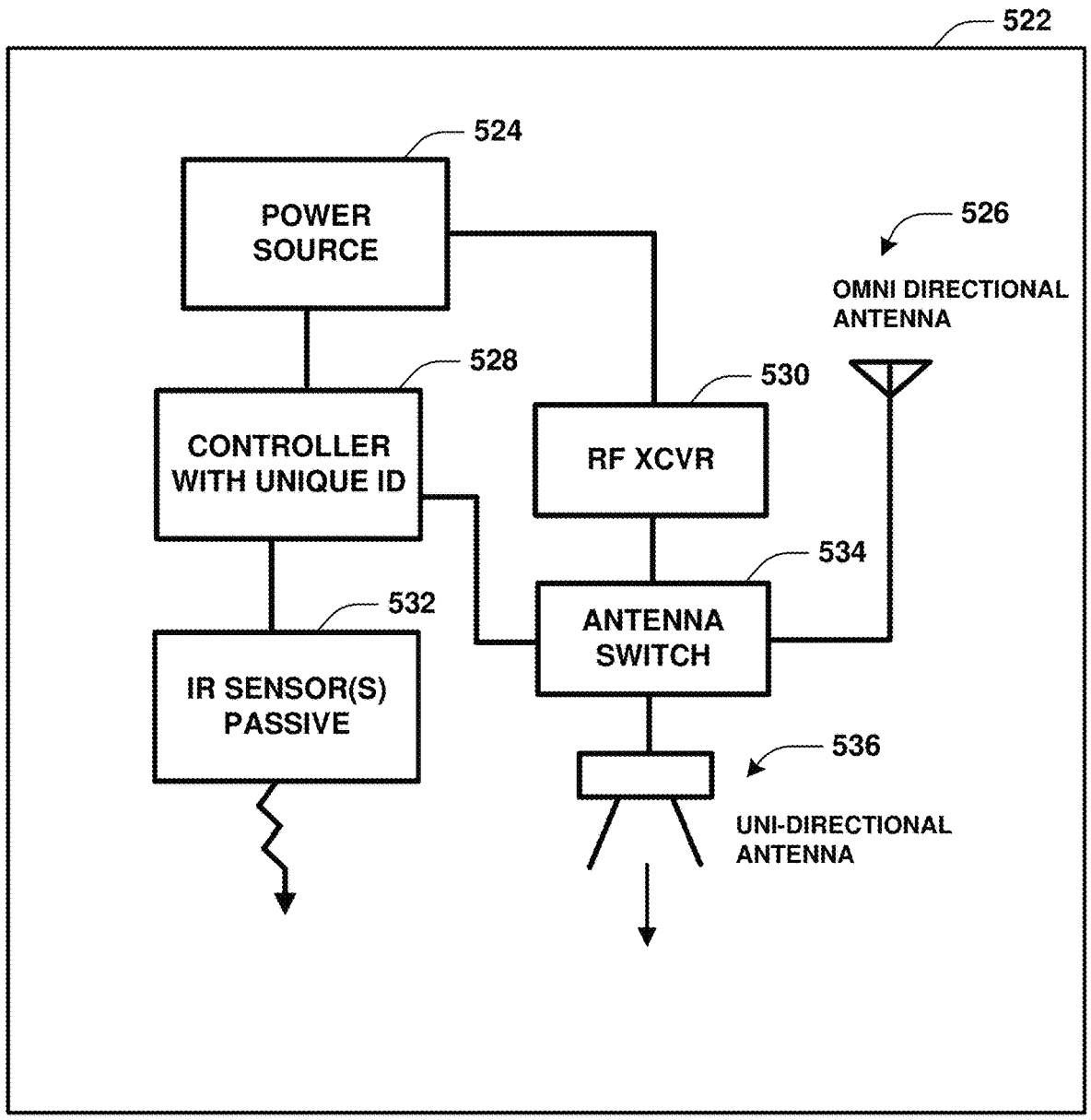
FIG. 5B is a component block diagram illustrating an example of a second component, of a wireless system, configured for tracking room entries and/or room exits.
Figure 5C:
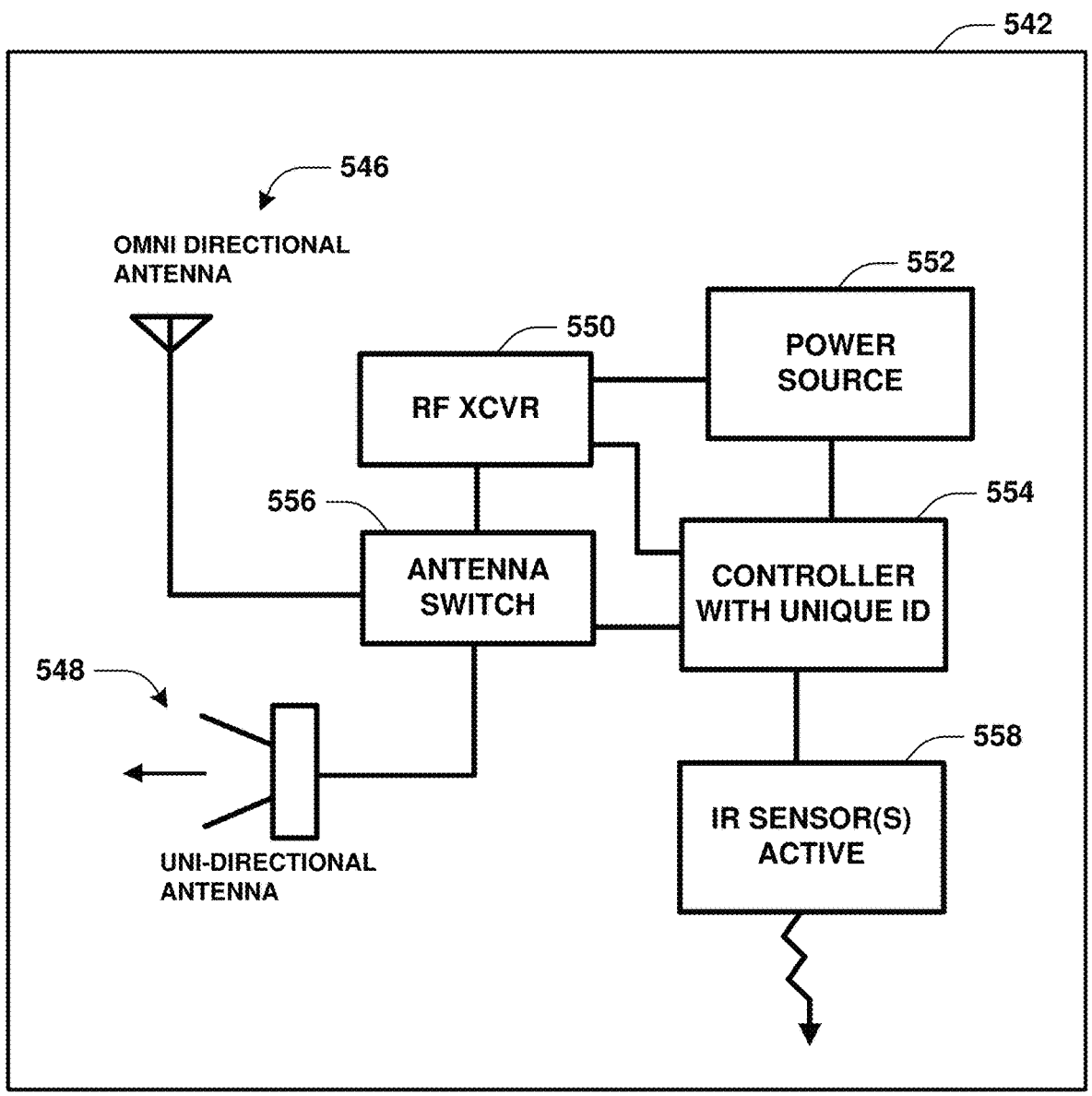
FIG. 5C is a component block diagram illustrating an example of a third component, of a wireless system, configured for tracking dispense device interactions.

FIGS. 5A-5C illustrate examples of components of the wireless system. FIG. 5A illustrates an example of a first component 502, of the wireless system, configured for assisting in tracking one or more entities. For example, the second device may comprise the first component 502. For example, the second device may comprise a motion and wear sensor 516 (e.g., the accelerometer and/or the one or more capacitance sensors). The second device may comprise a first power source 514 (e.g., a battery and/or a different type of power source). The second device may comprise a first controller device 512 (e.g., the first controller). The second identification number may be stored on the first controller device 512. The second device may comprise a first RF transceiver 510 (e.g., the second transceiver of the second device). In some examples, the first controller device 512 may be configured to activate the first RF transceiver 510 responsive to receiving one or more indications that the second device is moving and/or one or more indications that the second device is attached to the entity (e.g., from the motion and wear sensor 516).

The second device may comprise a first antenna switching device 508 (e.g., the first antenna switch). The second device may comprise a first antenna 504 (e.g., the second unidirectional antenna structure) and/or a second antenna 506 (e.g., the fourth unidirectional antenna structure). The first antenna switching device 508, the first controller device 512 and/or the first RF transceiver 510 may be configured to select an antenna (from the first antenna 504 and the second antenna 508) for transmission of a data packet based upon which antenna of the first antenna 504 and/or the second antenna 506 received a corresponding inquiry. In some examples, the motion and wear sensor 516, the first controller device 512, the first power source 514, the first RF transceiver 510, the first antenna switching device 508, the first antenna 504 and/or the second antenna 506 may be connected to each other according to FIG. 5A, using printed circuit board (PCB) methods. It may be appreciated that manufacturing the first component 502 of the wireless system using one or more PCBs may lead to greater manufacturing efficiency and/or lower costs.

FIG. 5B illustrates an example of a second component 522, of the wireless system, configured for tracking room entries and/or room exits. For example, the first device may comprise the second component 522. For example, the first device may comprise one or more first infrared sensors 532 (e.g., the first infrared sensor). The one or more first infrared sensors 532 may comprise one or more passive infrared sensors configured to monitor the first location. The first device may comprise a second power source 524 (e.g., a battery and/or a different type of power source). The first device may comprise a second controller device 528 (e.g., the second controller). The first identification number may be stored on the second controller device 528. The first device may comprise a second RF transceiver 530 (e.g., the first transceiver of the first device).

The first device may comprise a second antenna switching device 534 (e.g., a second antenna switch of the first device). The first device may comprise a third antenna 536 (e.g., the first unidirectional antenna structure) and/or a fourth antenna 526 (e.g., the first omnidirectional antenna structure). The second antenna switching device 534, the second controller device 528 and/or the second RF transceiver 530 may be configured to select the third antenna 536 for transmission of inquiries to badges (e.g., such as the second device) and/or select the fourth antenna 536 for transmission of messages to the data collection device and/or one or more repeater devices. In some examples, the one or more first infrared sensors 532, the second power source 524, the second controller device 528, the second RF transceiver 530, the second antenna switching device 534, the third antenna 536 and/or the fourth antenna 526 may be connected to each other according to FIG. 5B, using PCB methods. It may be appreciated that manufacturing the second component 522 of the wireless system using one or more PCBs may lead to greater manufacturing efficiency and/or lower costs.

FIG. 5C illustrates an example of a third component 542, of the wireless system, configured for tracking dispense device interactions. For example, the third device may comprise the third component 542. For example, the third device may comprise one or more second infrared sensors 558 (e.g., the second infrared sensor). The one or more second infrared sensors 558 may comprise one or more active infrared sensors configured to monitor the second location. The third device may comprise a third power source 552 (e.g., a battery and/or a different type of power source). The third device may comprise a third controller device 554 (e.g., the third controller). The third identification number may be stored on the third controller device 554. The third device may comprise a third RF transceiver 550 (e.g., the third transceiver of the third device).

The third device may comprise a third antenna switching device 556 (e.g., a third antenna switch of the third device). The third device may comprise a fifth antenna 548 (e.g., the third unidirectional antenna structure) and/or a sixth antenna 546 (e.g., the second omnidirectional antenna structure). The third antenna switching device 556, the third controller device 554 and/or the third RF transceiver 550 may be configured to select the fifth antenna 548 for transmission of inquiries to badges (e.g., such as the second device) and/or select the sixth antenna 546 for transmission of messages to the data collection device and/or one or more repeater devices. In some examples, the one or more second infrared sensors 558, the third power source 552, the third controller device 554, the third RF transceiver 550, the third antenna switching device 556, the fifth antenna 548 and/or the sixth antenna 546 may be connected to each other according to FIG. 5C, using PCB methods. It may be appreciated that manufacturing the third component 542 of the wireless system using one or more PCBs may lead to greater manufacturing efficiency and/or lower costs.

In some examples, the first device (e.g., the first event counter) may be a room event counter (e.g., a device configured for tracking entries into rooms and/or exits from rooms) and/or the third device may be a dispense device event counter (e.g., a device configured for tracking dispense device interactions). In some examples, a building (e.g., of the healthcare facility, the company, etc.) may comprise a plurality of room event counters and/or a plurality of dispense device event counters. Each room event counter may be comprised within a room of a plurality of rooms of the building (e.g., wherein each room of the plurality of rooms comprises a room event counter of the plurality of room event counters). In some examples, the plurality of rooms may comprise every room, some rooms, every sanitation room, some sanitation rooms, every hallway, some hallways, etc. of the building.

Alternatively and/or additionally, each dispense device event counter of the plurality of dispense device event counters may be comprised within and/or coupled to a dispense device of a plurality of dispense devices of the building (e.g., wherein each dispense device of the plurality of dispense devices may comprise and/or be coupled to a dispense device event counter of the plurality of dispense device event counters). In some examples, each room event counter of the plurality of room event counters may be assigned to a specific data collection device (e.g., and/or may transmit messages to the specific data collection device) of a plurality of data collection devices. Alternatively and/or additionally, each dispense device event counter of the plurality of dispense device event counters may be assigned to a specific data collection device of the plurality of data collection devices.

In some examples, a first set of room event counters of the plurality of room event counters and/or a first set of dispense device event counters of the plurality of dispense device event counters may be assigned to a first data collection device. The first set of room event counters and/or the first set of dispense device event counters may be located in a first part of the building (e.g., a first floor of the building, a first set of rooms of the building, etc.). Alternatively and/or additionally, a second set of room event counters of the plurality of room event counters and/or a second set of dispense device event counters of the plurality of dispense device event counters may be assigned to a second data collection device. The second set of room event counters and/or the second set of dispense device event counters may be located in a second part of the building.

In some examples, a number of devices (e.g., room event counters and/or dispense device event counters) assigned to a data collection device and/or a proximity of the data collection device to the devices assigned to the data collection device may be configured to ensure reception of transmissions performed by the devices and/or to optimize power usages of the devices in performing the transmissions. In some examples, each data collection device of the plurality of data collection devices may transmit messages to the data processing station (e.g., and/or a second data processing station). For example, the plurality of data collection devices may transmit messages to the data processing station using an Ethernet connection (e.g., and/or a different type of network connection).

Figure 8:
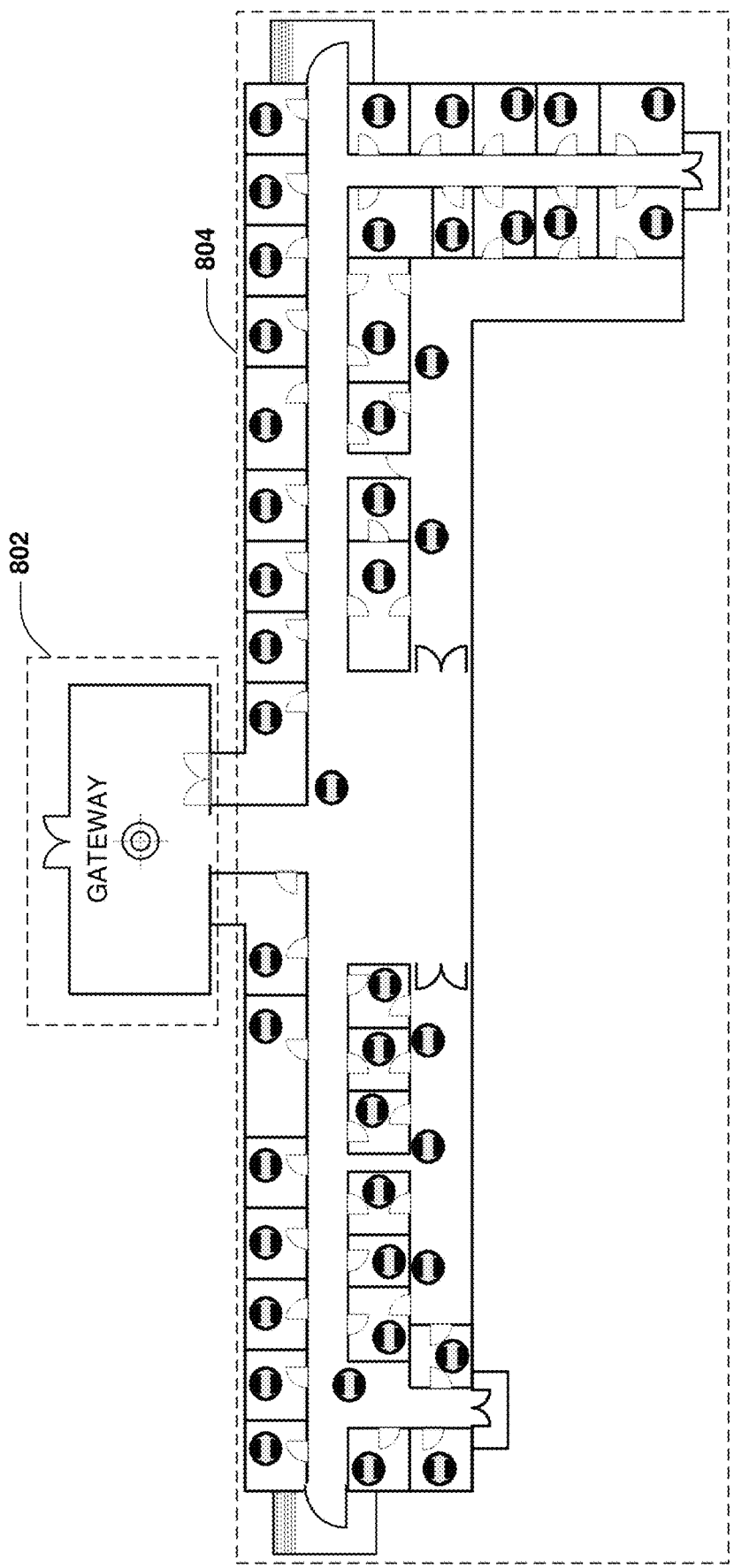
FIG. 8 is a component block diagram illustrating an example of a first set of devices assigned to a first data collection device.

FIG. 8 illustrates an example of a first set of devices 804 assigned to the first data collection device. For example, the first data collection device may comprise a gateway 802 of which the first set of devices 804 are configured to transmit messages to. For example, the first set of devices 804 may comprise the first set of room event counters and/or the first set of dispense device event counters. The first set of devices 804 may be located on the first floor of the building. In some examples, the gateway 802 may be connected to the Ethernet connection and/or a different type of network connection.

In some examples, each device of the first set of devices 804 may transmit messages to the first data collection device using one or more channels of a set of channels of the UHF band (and/or a different band). In some examples, the first data collection device may select and/or change one or more channels used by each device of the first set of devices 804. For example, the first data collection device may assign one or more channels to each device of the first set of devices 804. In some examples, the first data collection device may moderate usage of the set of channels amongst the first set of devices 804 in order to mitigate multipath effects.

In some examples, the first set of room event counters and/or the first set of dispense device event counters may be configured to transmit messages (e.g., directly) to the first data collection device. Alternatively and/or additionally, the first set of room event counters and/or the first set of dispense device event counters may be configured to transmit messages through one or more repeater devices to the first data collection device.

Figure 9:
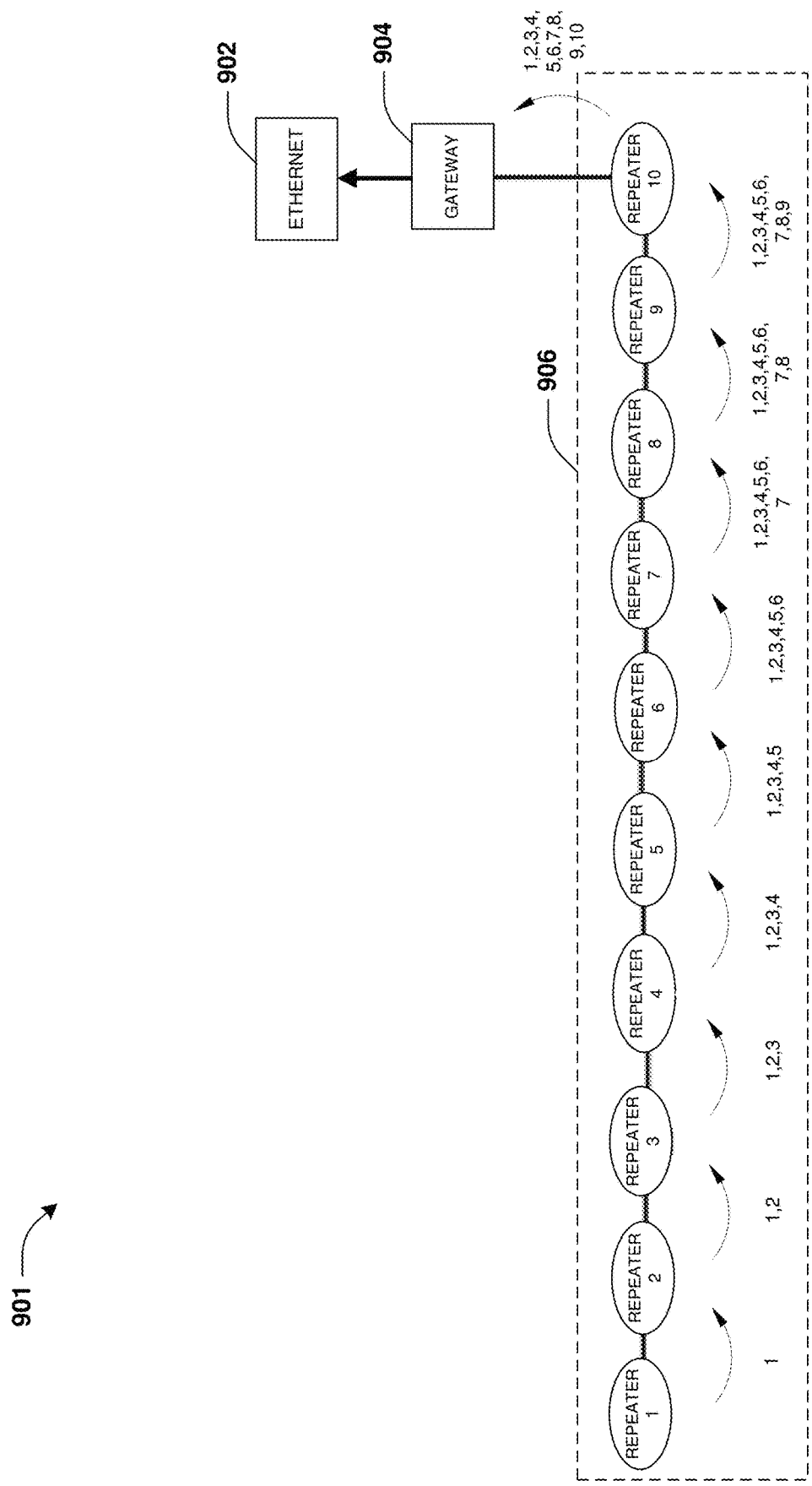
FIG. 9 is a component block diagram illustrating an example of using a set of repeater devices to transmit one or more messages to a gateway.

FIG. 9 illustrates an example of using a set of repeater devices 906 to transmit one or more messages to a gateway 904 (e.g., the first data collection device). For example, one or more messages may be transmitted by a room event counter of the first set of room event counters and/or a dispense device event counter of the first set of dispense device event counters to a first repeater device "REPEATER 1" of the set of repeater devices 906. The one or more messages may be relayed across repeater devices of the first set of repeater devices 906 until the one or more messages are transmitted to the gateway 904.

The gateway 904 may transmit the one or more messages to the data processing station using an Ethernet connection 902 (and/or a different type of network connection). In some examples, repeater devices of the set of repeater devices may be comprised within room event counters of the first set of room event counters and/or dispense device event counters of the first set of dispense device event counters. Alternatively and/or additionally, repeater devices of the first set of repeater devices may be stand-alone devices located in hallways, rooms, etc. of the building (e.g., in the first floor of the building).

Figure 10:
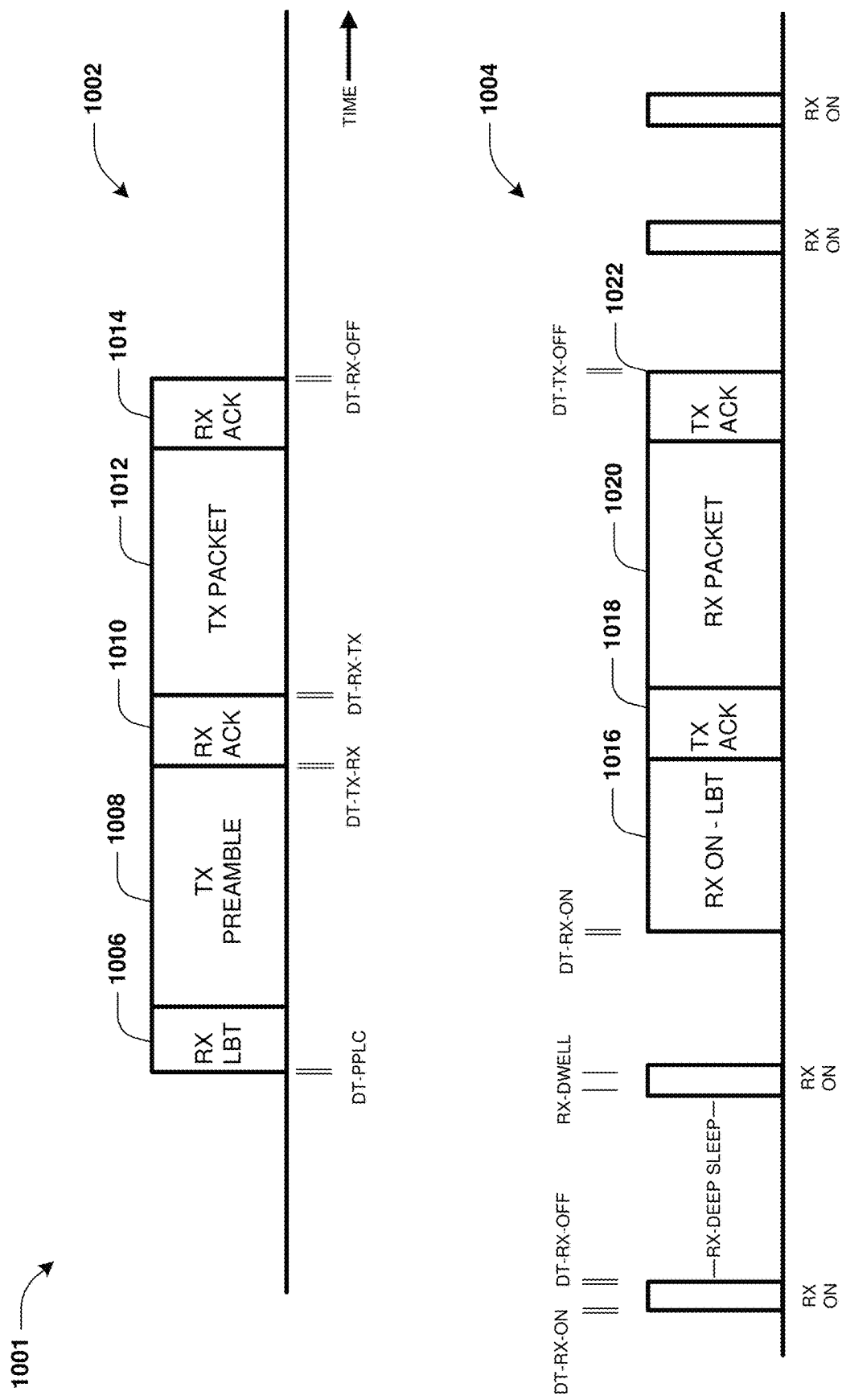
FIG. 10 is an illustration of an example of a timing diagram of a fifth device transmitting a fourth message to a sixth device.

FIG. 10 illustrates an example of a timing diagram 1001 of a fifth device transmitting a fourth message to a sixth device. For example, the fifth device may comprise a room event counter and/or a dispense device event counter. Alternatively and/or additionally, the sixth device may comprise a repeater device (and/or a data collection device). In some examples, a first portion 1002 of the timing diagram 1001 may illustrate activity by the fifth device and/or a second portion 1004 of the timing diagram 1001 may illustrate activity by the sixth device.

In some examples, the fourth message may be generated based upon a fourth event. For example, the fourth message may comprise a fourth identification number associated with a second badge configured for assisting in tracking events associated with a second entity, a fourth time value, a fifth identification number associated with the fifth device and/or an indication of a type of event of the fourth event (e.g., a direction of motion). In some examples, the fifth device may use an LBT system. For example, prior to transmitting the fourth message, the fifth device may listen to one or more channels of the wireless system (at RX LBT 1006). Responsive to determining that the one or more channels are not being used, the fifth device may transmit a preamble to the sixth device (at TX PREAMBLE 1008). A length of the preamble may be configured such that the sixth device may receive the preamble (at RX ON-LBT 1016) and/or may determine that the fifth device will transmit the fourth message.

Responsive to receiving the preamble, the sixth device may transmit a first acknowledgment message (at TX ACK 1018) and/or the fifth device may receive the first acknowledgement message (at RX ACK 1010). The fifth device may transmit the fourth message (at TX PACKET 1012) and/or the sixth device may receive the fourth message (at RX PACKET 1020). Responsive to receiving the fourth message, the sixth device may transmit a second acknowledgment message (at TX ACK 1022) and/or the fifth device may receive the second acknowledgement message (at RX ACK 1014).

Figure 11:
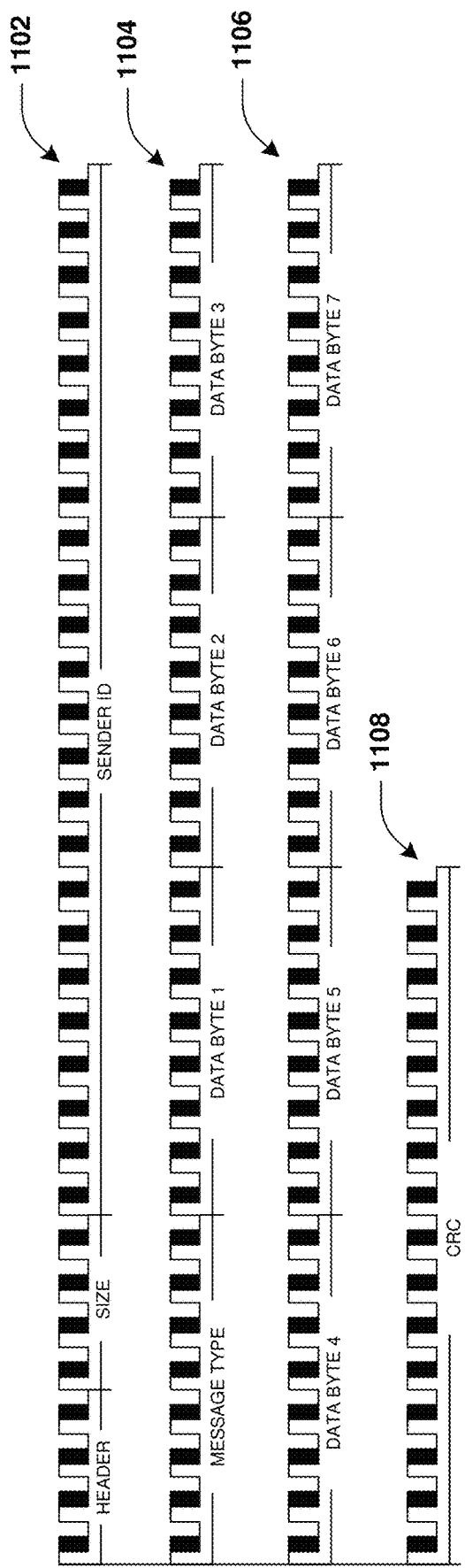
FIG. 11 is a diagram illustrating an example of a fourth message.

FIG. 11 illustrates an example of the fourth message. For example, the fourth message may comprise a first section 1102 of the fourth message, a second section 1104 of the fourth message, a third section 1106 of the fourth message and/or a fourth section 1108 of the fourth message. The first section 1102 may comprise a header, a size and/or the fifth identification number (SENDER ID) associated with the fifth device. Alternatively and/or additionally, the second section 1104 may comprise a message type, a first data byte, a second data byte and/or a third data byte. Alternatively and/or additionally, the third section 1106 may comprise a fourth data byte, a fifth data byte, a sixth data byte and/or a seventh data byte. In some examples, the fourth identification number and/or a time value may be comprised within the first data byte, the second data byte, the third data byte, the fourth data byte, the fifth data byte, the sixth data byte and/or the seventh data byte. In some examples, the fourth section 1108 may comprise a cyclic redundancy check (CRC) and/or a different type of error detecting code.

In some examples, the plurality of dispense device event counters may comprise a set of portable dispense device event counters. For example, each portable dispense device event counter of the set of portable dispense device event counters may be comprised within a portable dispense device of a set of portable dispense devices. Accordingly, locations of the set of portable dispense device event counters may be changed (e.g., portable dispense device event counters may be carried from a first part of the building to a second part of the building). In some examples, the locations of the portable dispense device event counters may be determined using room event counters of the plurality of room event counters.

In some examples, a first portable dispense device event counter may be comprised within a first portable dispense device (e.g., portable soap dispenser, portable sanitation liquid dispenser, portable water dispenser, etc.). In some examples, the first portable dispense device may be associated with a fifth event where the first portable dispense device enters a second room (e.g., the portable dispense device may be carried into the second room). In some examples, a second room event counter may detect the fifth event.

In some examples, responsive to determining that the fifth event is associated with the first portable dispense device event counter entering the second room, the first portable dispense device event counter may be paired with the second room event counter. Alternatively and/or additionally, responsive to detecting a sixth event associated with the first portable dispense device event counter exiting the second room, the first portable dispense device event counter may be unpaired with the second room event counter.

Accordingly, while the first portable dispense device event counter is inside the second room, a location of the first portable dispense device event counter may be determined to be within the second room (e.g., by the data processing station). For example, while the first portable dispense device event counter is inside the second room, the first portable dispense device event counter may transmit messages associated with events to one or more repeater devices and/or one or more data collection devices comprising a sixth identification number associated with the second room event counter. Alternatively and/or additionally, responsive to the first portable dispense device event counter being paired with the second room event counter, the second room event counter may transmit a fifth message to one or more repeater devices and/or one or more data collection devices. The fifth message may comprise an indication that the first portable dispense device event counter is paired with the second room event counter and/or that the first portable dispense device event counter has entered the second room (and/or is in the second room). Alternatively and/or additionally, responsive to the first portable dispense device event counter being unpaired with the second room event counter, the second room event counter may transmit a sixth message to one or more repeater devices and/or one or more data collection devices. The sixth message may comprise an indication that the first portable dispense device event counter is not paired with the second room event counter and/or that the first portable event counter has exited the second room (and/or is not in the second room). For example, the first portable dispense device event counter may be moved from the second room to a third room and may be paired with a third room event counter associated with the third room.

Figure 12:
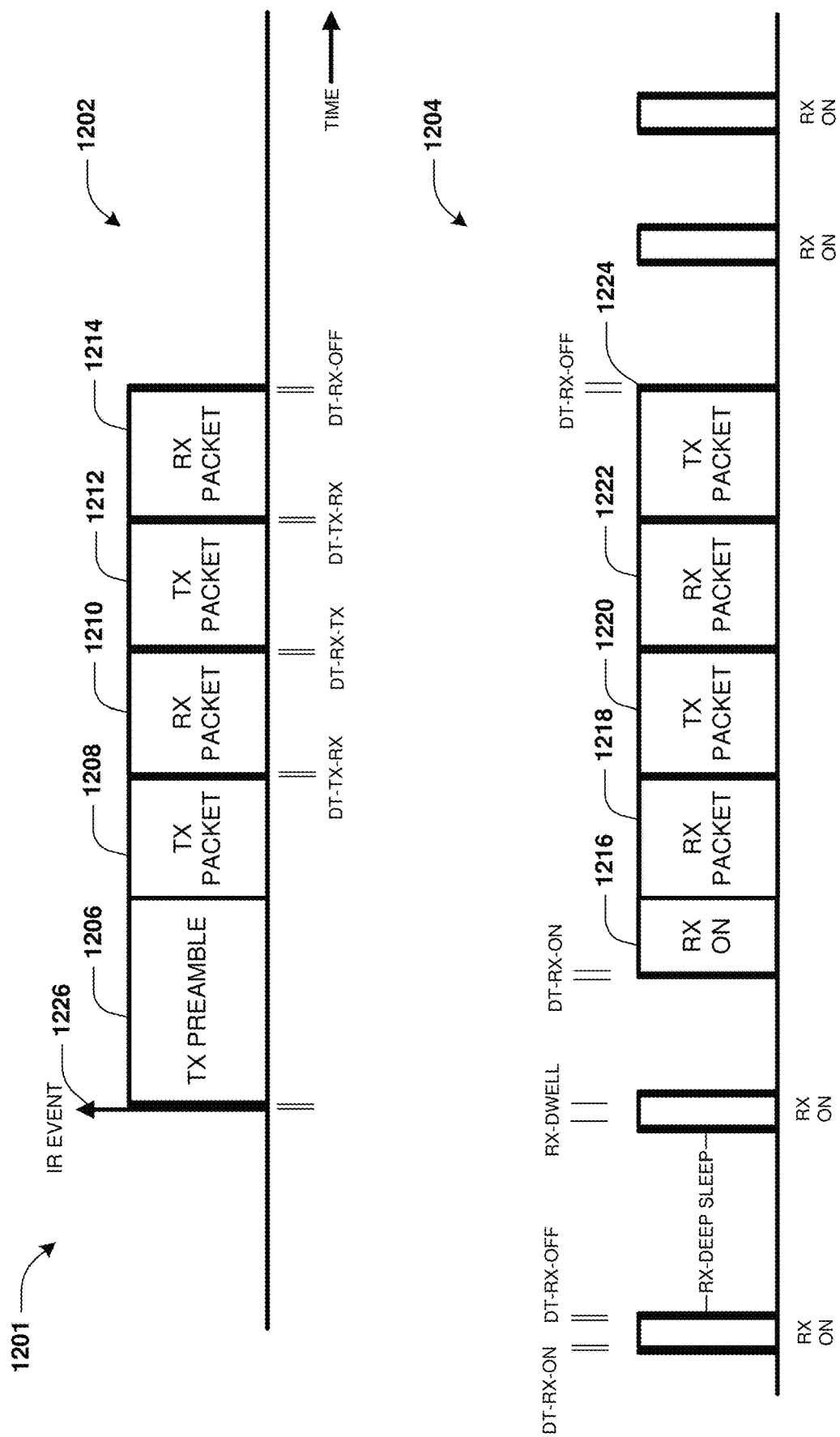
FIG. 12 is an illustration of an example of a timing diagram of a second room event counter interacting with a first portable dispense device event counter responsive to detecting a fifth event.

FIG. 12 illustrates an example of a timing diagram 1201 of the second room event counter interacting with the first portable dispense device event counter responsive to detecting the fifth event. For example, a first portion 1202 of the timing diagram 1201 may illustrate activity by the second room event counter and/or a second portion 1204 of the timing diagram 1201 may illustrate activity by the first portable dispense device event counter.

For example, responsive to the second room event counter detecting the fifth event (at IR EVENT 1226), the second room event counter may transmit a second preamble to the first portable dispense device event counter (at TX PREAMBLE 1206). A length of the second preamble may be configured such that the first portable dispense device event counter may receive the second preamble (at RX ON 1216) and/or may determine that the first room event counter will transmit a fourth inquiry. The fourth inquiry may be a data packet. The second room event counter may transmit the fourth inquiry (at TX PACKET 1208) and/or the first portable dispense device event counter may receive the fourth inquiry (at RX PACKET 1218).

Figure 13:
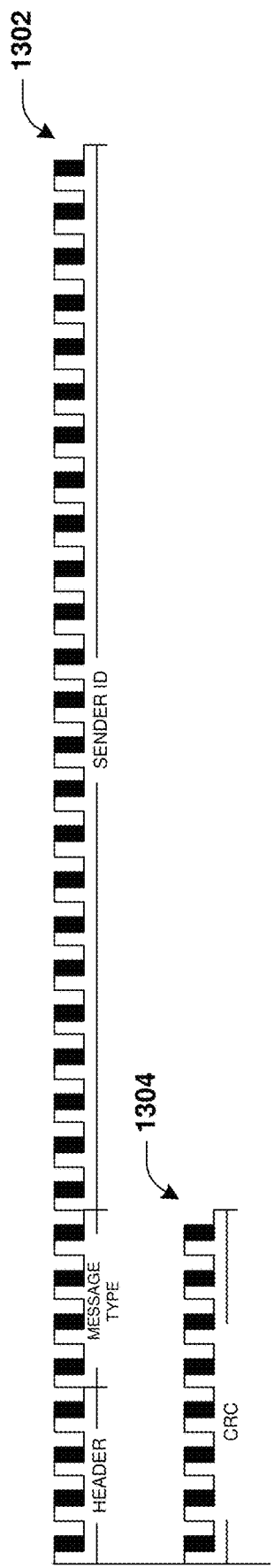
FIG. 13 is a diagram illustrating an example of a fourth inquiry.

FIG. 13 illustrates an example of the fourth inquiry. For example, the fourth inquiry may comprise a first section 1302 of the fourth inquiry and/or a second section 1304 of the fourth inquiry. For example, the first section 1302 may comprise a header, a message type (e.g., comprising a direction of motion associated with the fifth event) and/or the sixth identification number (SENDER ID). Alternatively and/or additionally, the second section 1304 may comprise a CRC and/or a different type of error detecting code.

Responsive to receiving the third inquiry, the first portable dispense device event counter may transmit a fourth data packet (at TX PACKET 1220) and/or the second room event counter may receive the fourth data packet (at RX PACKET 1210). The first portable dispense device may transmit the fourth data packet responsive to determining that a fifth signal strength of the third inquiry is greater than a fifth signal strength threshold. In some examples, the fourth data packet may comprise a seventh identification number associated with the first portable dispense device event counter and/or a third RSSI comprising an indication of the fifth signal strength.

In some examples, responsive to receiving the fourth data packet, the second room event counter may transmit a fifth data packet (at TX PACKET 1212) and/or the first portable dispense device event counter may receive the fifth data packet (at RX PACKET 1222). The second room event counter may transmit the fifth data packet responsive to determining that a sixth signal strength of the fifth data packet is greater than a sixth signal strength threshold. In some examples, the sixth signal strength threshold may be the same as the fifth signal strength threshold. In some examples, responsive to determining that the sixth signal strength of the fifth data packet is greater than the sixth signal strength threshold and/or that the direction of motion of the fifth event is associated with the first portable dispense device event counter entering the second room, the second room event counter may be paired with the first portable dispense device event counter.

Figure 14:
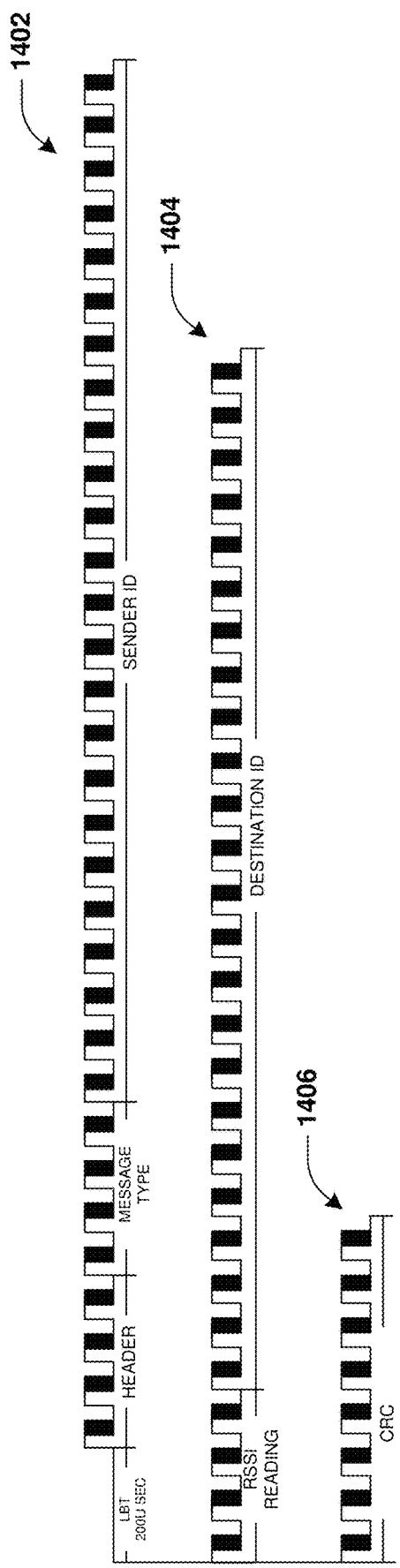
FIG. 14 is a diagram illustrating an example of a fifth data packet.

FIG. 14 illustrates an example of the fifth data packet. For example, the fifth data packet may comprise a first section 1402 of the fifth data packet, a second section 1404 of the fifth data packet and/or a third section 1406 of the fifth data packet. The first section 1402 may comprise a second header, a second message type (e.g., comprising the direction of motion associated with the fifth event and/or pairing status associated with the second room event counter being paired with the first portable dispense device event counter) and/or the sixth identification number (SENDER ID). Alternatively and/or additionally, the second section 1404 may comprise a fourth RSSI comprising an indication of the sixth signal strength and/or the seventh identification number. Alternatively and/or additionally, the third section 1406 may comprise a CRC and/or a different type of error detecting code.

In some examples, responsive to receiving the fifth data packet, the first portable dispense device event counter may transmit a sixth data packet (at TX PACKET 1224) and/or the second room event counter may receive the sixth data packet (at RX PACKET 1214). In some examples, the sixth data packet may comprise pairing information associated with the first portable dispense device event counter being paired with the second room event counter.

Figure 6A:
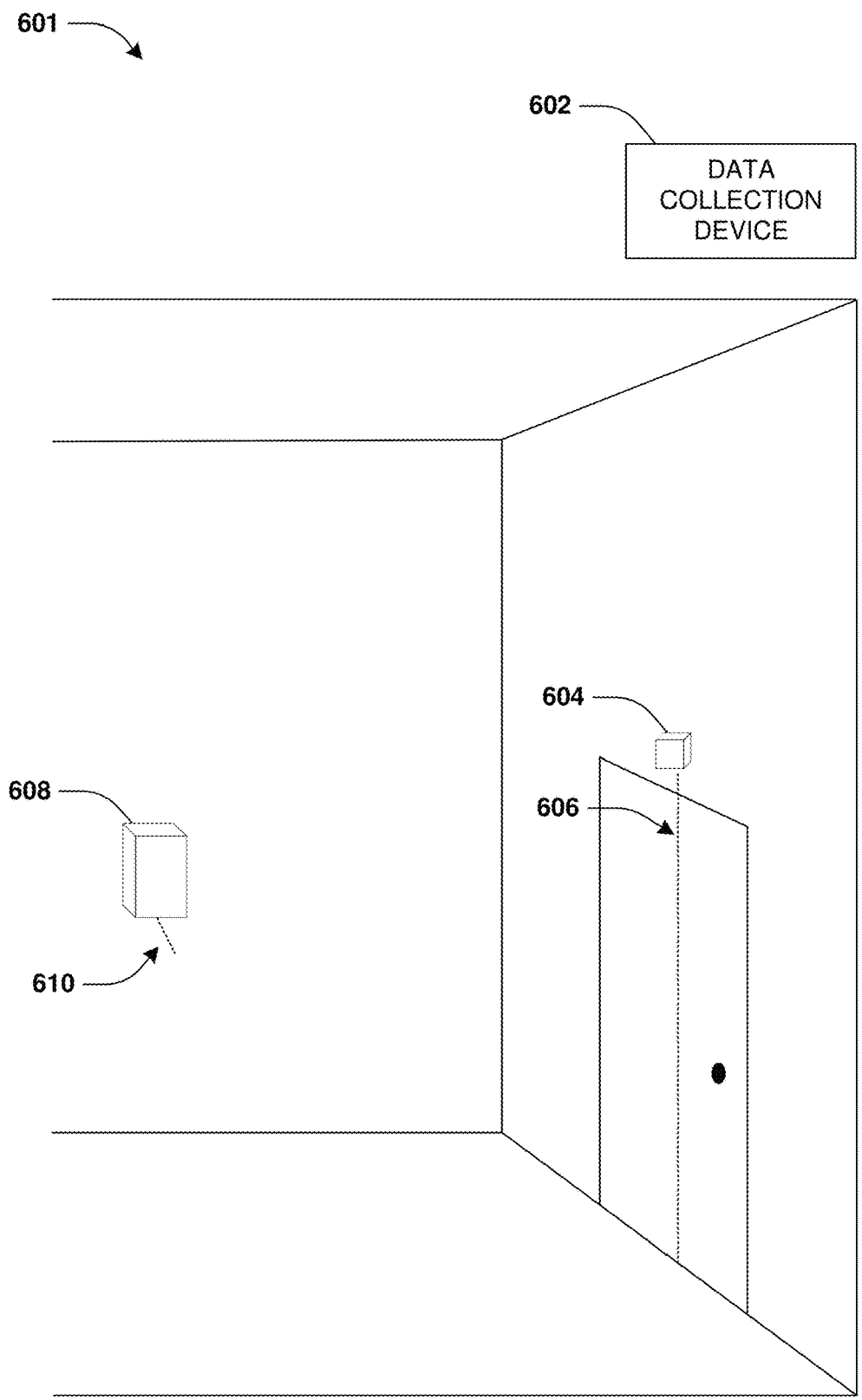
FIG. 6A is a component block diagram illustrating an example system for determining a time-length of an action, where the example system comprises a first event counter and a second event counter.
Figure 6B:
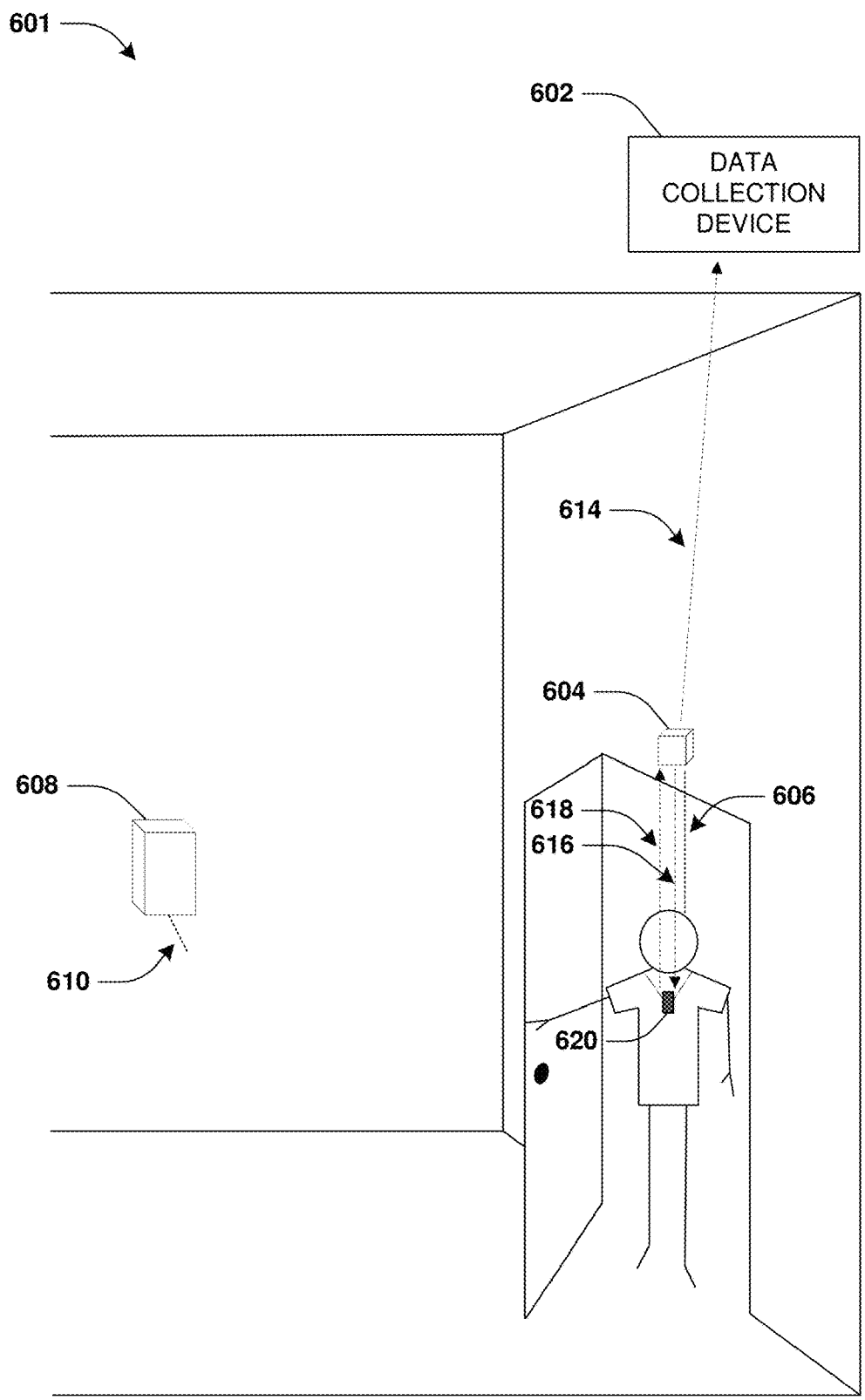
FIG. 6B is a component block diagram illustrating an example system for determining a time-length of an action, where a first event counter receives a first data packet, associated with a first event.
Figure 6C:
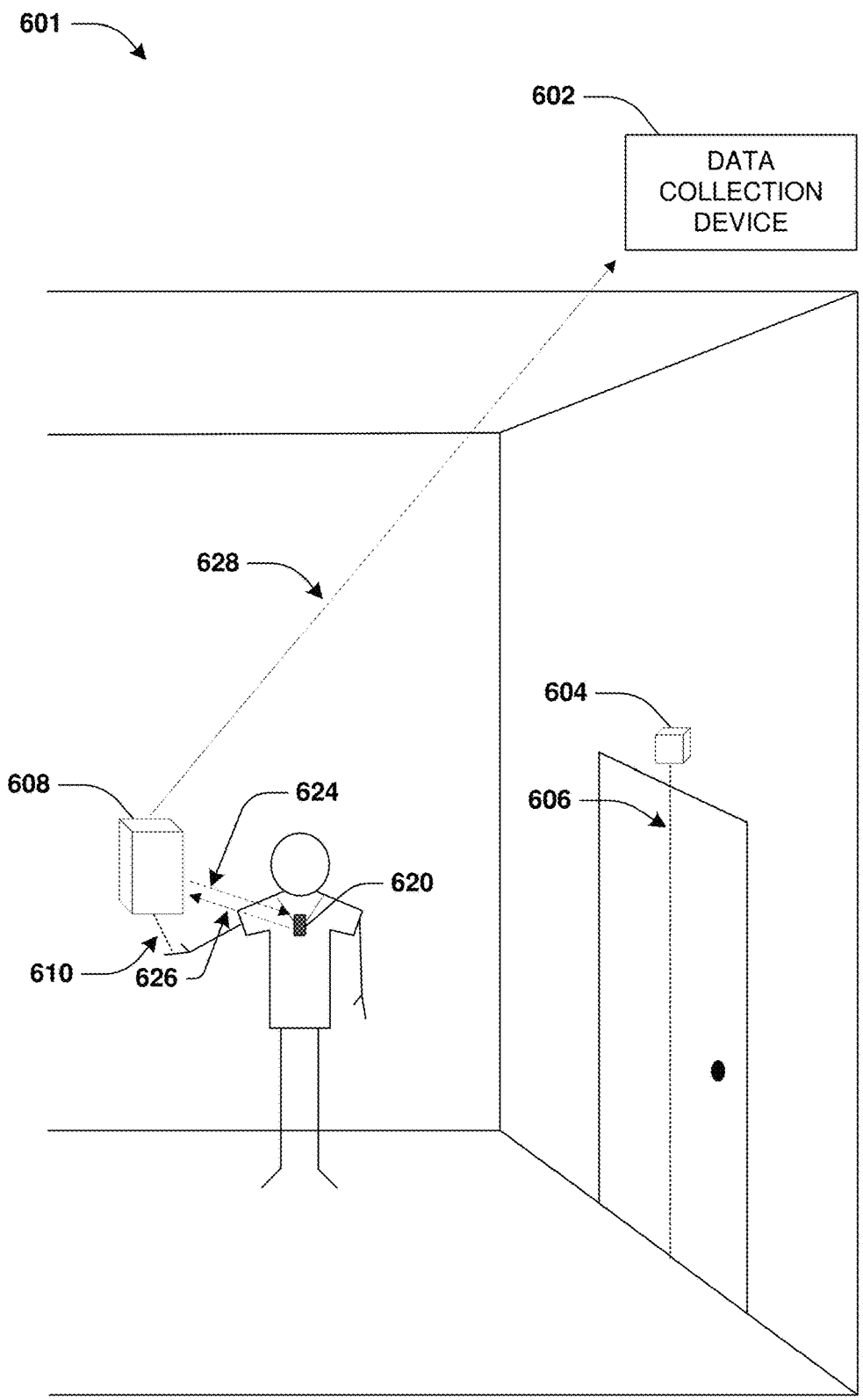
FIG. 6C is a component block diagram illustrating an example system for determining a time-length of an action, where a second event counter receives a second data packet, associated with a second event.

FIGS. 6A-6C illustrate examples of a system 601 for determining a time-length of an action. FIG. 6A illustrates a first event counter 604 and a second event counter. The first event counter 604 may be associated with a first identification number. The second event counter may be comprised within a dispense device 608. A first infrared sensor may be comprised within the first event counter 604 and/or may be coupled to the first event counter 604. The first infrared sensor may be configured to monitor a first location 606. A second infrared sensor may be comprised within the second event counter and/or may be coupled to the second event counter. The second infrared sensor may be configured to monitor a second location 610.

FIG. 6B illustrates the first event counter 604 receiving a first reply data packet 618, associated with a first event. In some examples, the first event may comprise an entity entering a room. The first event may be detected by receiving an indication of motion (e.g., by the entity) at the first location 606 from the first infrared sensor. Responsive to detecting the first event, a first device (e.g., comprising an RF module) may be activated. Responsive to activating the first device, a first inquiry 616 may be transmitted by the first device in a first direction. A badge 620, comprising a second device, may be assigned and/or attached to (e.g., worn by, held by, etc.) the entity.

The second device (e.g., comprising an RF module) may receive the first inquiry 616 via the first direction. Responsive to receiving the first inquiry 616, the second device may transmit the first reply data packet 618 to the first device (e.g., comprised within the first event counter 604 and/or coupled to the first event counter 604). The first reply data packet 618 may comprise a second identification number associated with the second device (e.g., and/or the badge 620). The first device may generate a first message 614 based upon the first reply data packet 618. The first message 614 may comprise the second identification number (e.g., associated with the second device), a first time value and/or the first identification number associated with the first device. The first time value may correspond to a first time that the first reply data packet 618 was transmitted by the second device and/or received by the first device. In some examples, the first message 614 may comprise an indication of the first event (e.g., a direction of motion and/or that the room was entered by the entity). The first device may transmit the first message 614 to a data collection device 602 and/or one or more first repeater devices. In some examples, rather than the first message 614 comprising the first time value, a first timestamp may be assigned to the first message 614 by the one or more first repeater devices and/or by the data collection device 602 upon receipt of the first message 614.

FIG. 6C illustrates the second event counter (e.g., comprised within the dispense device 608) receiving a second reply data packet 626, associated with a second event. In some examples, the second event may comprise the entity interacting with the dispense device 608. The second event may be detected by receiving an indication of motion (e.g., by the entity) at the second location 610 from the second infrared sensor. Responsive to detecting the second event, a third device (e.g., comprising an RF module) may be activated. Responsive to activating the third device, a second inquiry 624 may be transmitted by the third device in a second direction. The second device (e.g., comprised within the badge 620) may receive the second inquiry 624 via the second direction. Responsive to receiving the second inquiry 624, the second device may transmit the second reply data packet 626 to the third device (e.g., comprised within the dispense device 608 and/or coupled to the dispense device 608). The second reply data packet 626 may comprise the second identification number (e.g., associated with the second device) and/or a second counter value corresponding to a second time that the second device transmits the second reply data packet 626.

The third device may generate a second message 628 based upon the second reply data packet 626. The second message 628 may comprise the second identification number (e.g., associated with the second device), a second time value and/or a third identification number associated with the third device. In some examples, the second time value may correspond to a second time that the second reply data packet 626 was transmitted by the second device and/or received by the third device. The third device may transmit the second message 628 to the data collection device 602 and/or one or more second repeater devices. In some examples, rather than the second message 628 comprising the second time value, a second timestamp may be assigned to the second message 628 by the one or more second repeater devices and/or by the data collection device 602 upon receipt of the second message 628.

In some examples, the data collection device 602 may transmit the first message 614 and/or the second message 628 to a data processing station. In some examples, the data processing station may generate a time-length of an action based upon an evaluation of the first time value (and/or the first timestamp) and/or the second time value (and/or the second timestamp). The action may comprise the entity entering the room and interacting with the dispense device 608.

Figure 7:
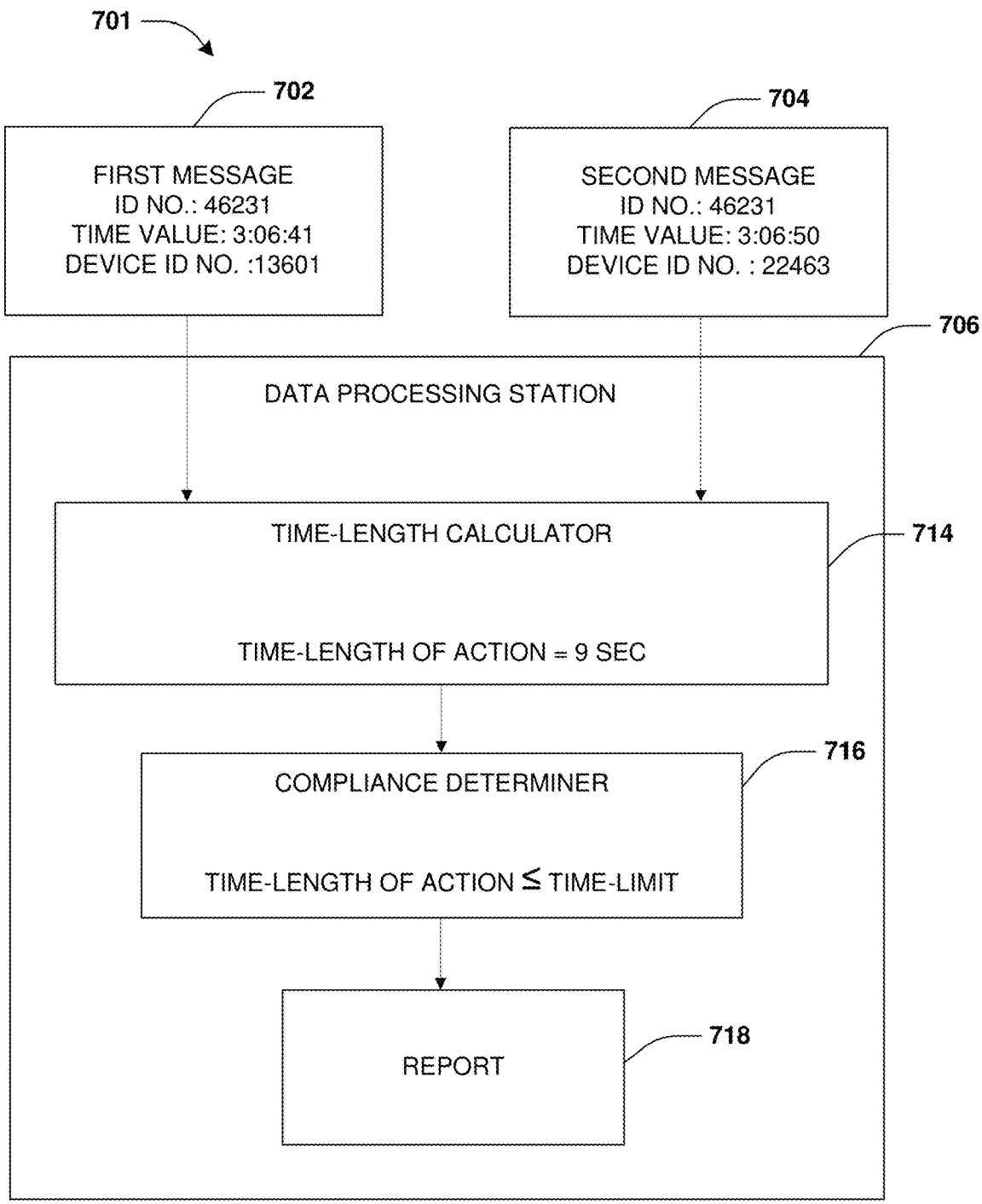
FIG. 7 is a component block diagram illustrating an example system for determining a time-length of an action and/or determining compliance with a protocol based upon the time-length of the action.

FIG. 7 illustrates an example of a system 701 for determining a time-length of an action and/or determining compliance with a protocol based upon the time-length of the action. A first message 702 associated with a first event may be received by a data processing station 706. The first event may comprise an entity entering a room. In some examples, the first message 702 may comprise an identification number "46231" associated with a first device. The first device may be comprised within a badge assigned to the entity. The first message 702 may comprise a first time value "3:06:41" corresponding to a first time of the first event and/or a second identification number "13601" corresponding to a second device that generated the first message 702. A second message 704 associated with a second event may be received by the data processing station 706. The second event may comprise the entity interacting with a dispense device. In some examples, the second message 704 may comprise the identification number "46231", a second time value "3:06:50" corresponding to a second time of the second event and/or a third identification number "22463" corresponding to a third device that generated the second message 704.

In some examples, a time-length calculator 714 may determine the time-length of the action to be 9 seconds. For example, the time-length of the action may be determined by performing an (e.g., mathematical) operation on the first time value "3:06:41" and/or the second time value "3:06:50".

In some examples, a compliance determiner 716 may determine compliance with a protocol of a healthcare facility (e.g., and/or a company). For example, the healthcare facility may have the protocol for (e.g., the entity) entering the room and interacting with the dispense device. The protocol may require a time-limit between entering the room and interacting with the dispense device. The compliance determiner 716 may determine compliance with the protocol by comparing the time-length of the action with the time-limit. In an example, the time-limit associated with the protocol may be 7 seconds. Accordingly, the compliance determiner 716 may determine that the time-length of the action (e.g., 9 seconds) is not compliant with the protocol. In a second example, the time-limit associated with the protocol may be 10 seconds. Accordingly, the compliance determiner 716 may determine that the time-length of the action (e.g., 9 seconds) is compliant with the protocol. In some examples, a report 718 may be generated (e.g., by the data processing station 706) comprising the identification number, the time-length of the action and/or the compliance (e.g., with the protocol).

In some examples, responsive to determining that the time-length of the action is not compliant with the protocol, the report 718 may be generated and/or transmitted to the corresponding entity and/or a manager associated with the corresponding entity. For example, the report 718 may be transmitted as part of instructions causing a graphical user interface of a display of a device of the corresponding entity and/or the manager to display at least some of the report 718 and/or a warning to modify behavior. Transmission of the instructions may be controlled to cause reports to be sent to (e.g., only) devices associated with entities that do not comply with the protocol at least a threshold amount.

It may be appreciated that the disclosed subject matter may assist in determining compliance with a protocol by an entity and/or in determining a current location and/or a previous location of the entity.

Implementation of at least some of the disclosed subject matter may lead to benefits including, but not limited to, an increase in accuracy and/or precision of the determining the compliance with the protocol (e.g., as a result of event counters transmitting inquiries responsive to detecting events, as a result of the event counters transmitting the inquiries in a directional manner using unidirectional antenna structures, as a result of devices, comprised within badges configured for assisting in tracking events associated with entities, transmitting data packets to event counters responsive to receiving the inquiries, as a result of the devices transmitting the data packets in a directional manner using unidirectional antenna structures, as a result of determining the compliance with the protocol based upon the time-length of the action, as a result of implementing an LBT system to ensure reception of data packets and/or messages, as a result of transmitting data packets and/or messages periodically to ensure reception of the data packets and/or the messages, as a result of using an omnidirectional antenna structure to transmit messages to a data collection device and/or a data processing station, as a result of using repeater devices to relay information across devices to the data collection device and/or the data processing station, etc.).

Alternatively and/or additionally, implementation of at least some of the disclosed subject matter may lead to benefits including a reduction in (e.g., wireless) interference between (e.g., transmissions of) devices (e.g., as a result of event counters transmitting inquiries responsive to detecting events, as a result of devices, comprised within badges configured for assisting in tracking events associated with entities, transmitting data packets to event counters responsive to receiving the inquiries, as a result of the devices transmitting the data packets in a directional manner using unidirectional antenna structures, as a result of a data collection device moderating channels used by event counters for transmitting messages, etc.).

Alternatively and/or additionally, implementation of at least some of the disclosed subject matter may lead to benefits including a reduction in power usage (e.g., as a result of deactivating a device of a badge responsive to sensing the device is not moving, as a result of deactivating the device of the badge responsive to sensing that the device and/or the badge are not attached to the entity, as a result of the device of the badge transmitting data packets merely when inquiries are received, etc.).

In some examples, at least some of the disclosed subject matter may be implemented on a client device, and in some examples, at least some of the disclosed subject matter may be implemented on a server (e.g., hosting a service accessible via a network, such as the Internet).

Figure 15:
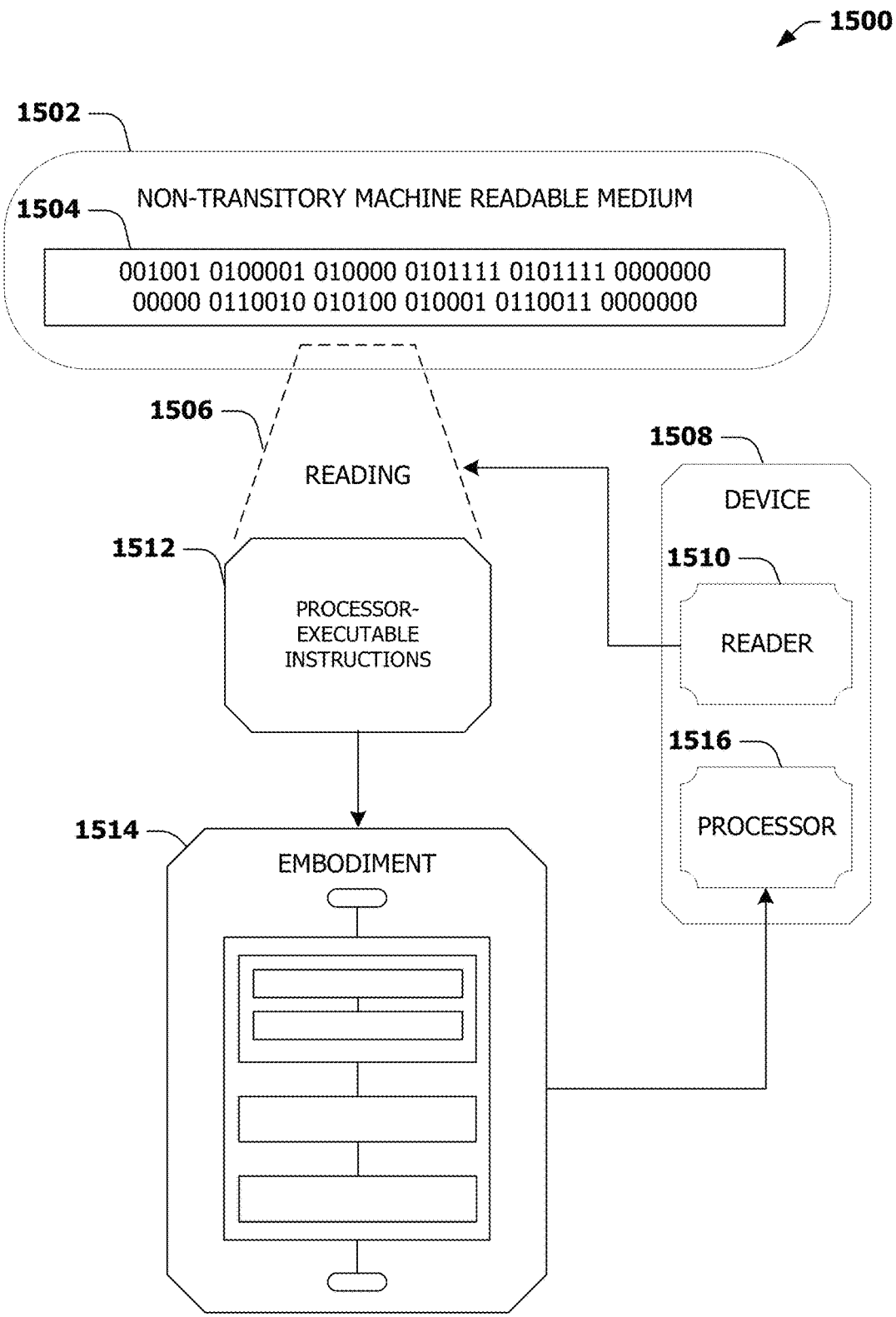
FIG. 15 is an illustration of a scenario featuring an example non-transitory machine readable medium in accordance with one or more of the provisions set forth herein.

FIG. 15 is an illustration of a scenario 1500 involving an example non-transitory machine readable medium 1502. The non-transitory machine readable medium 1502 may comprise processor-executable instructions 1512 that when executed by a processor 1516 cause performance (e.g., by the processor 1516) of at least some of the provisions herein (e.g., embodiment 1514).

The non-transitory machine readable medium 1502 may comprise a memory semiconductor (e.g., a semiconductor utilizing static random access memory (SRAM), dynamic random access memory (DRAM), and/or synchronous dynamic random access memory (SDRAM) technologies), a platter of a hard disk drive, a flash memory device, or a magnetic or optical disc (such as a compact disc (CD), digital versatile disc (DVD), or floppy disk).

The example non-transitory machine readable medium 1502 stores computer-readable data 1504 that, when subjected to reading 1506 by a reader 1510 of a device 1508 (e.g., a read head of a hard disk drive, or a read operation invoked on a solid-state storage device), express the processor-executable instructions 1512.

In some embodiments, the processor-executable instructions 1512, when executed, cause performance of operations, such as at least some of the example method 400 of FIG. 4, for example. In some embodiments, the processor-executable instructions 1512 are configured to cause implementation of a system, such as at least some of the example system of FIGS. 5A-5C, the example system 601 of FIGS. 6A-6C, the example system 701 of FIG. 7, the example system of FIG. 8, the example system of FIG. 9, the example system of FIG. 10, the example system of FIG. 11, the example system of FIG. 12, the example system of FIG. 13, and/or the example system of FIG. 14, for example.

As used in this application, "component," "module," "system", "interface", and/or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "example" is used herein to mean serving as an instance, illustration, etc., and not necessarily as advantageous. As used herein, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", and/or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Various operations of embodiments are provided herein. In an embodiment, one or more of the operations described may constitute computer readable instructions stored on one or more computer and/or machine readable media, which if executed will cause the operations to be performed. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein. Also, it will be understood that not all operations are necessary in some embodiments.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A system, comprising:
a first device, associated with a first identification number, comprising:
a first sensor configured to:
detect motion at a first location; and
a first transceiver configured to:
after the first sensor detects the motion at the first location, receive a first data packet from a second device, the first data packet comprising a second identification number associated with the second device; and
transmit a first message to a data processing station, the first message comprising the first identification number and the second identification number; and
a third device, associated with a third identification number, comprising:
a second sensor configured to:
detect motion at a second location; and
a second transceiver configured to:
after the second sensor detects the motion at the second location, receive a second data packet from the second device, the second data packet comprising the second identification number; and
transmit a second message to the data processing station, the second message comprising the second identification number and the third identification number.

2. The system of claim 1,
the first sensor comprising a first infrared sensor;
the motion detected at the first location by the first sensor associated with an entity entering a room;
the second sensor comprising a second infrared sensor; and
the motion detected at the second location by the second sensor associated with the entity interacting with a dispense device.

3. The system of claim 2,
the first message comprising an indication of a direction of motion of the motion detected at the first location, wherein the direction of motion is indicative of the entity entering the room.

4. The system of claim 1, the data processing station configured to generate a time-length of an action based upon an evaluation of the first message and the second message.

5. The system of claim 1, the data processing station configured to:
determine a first time associated with the first data packet;
determine a second time associated with the second data packet; and
generate a time-length of an action based upon an evaluation of the first time and the second time.

6. The system of claim 4, the data processing station configured to determine compliance with a protocol by comparing the time-length of the action with a time-limit associated with the protocol.

7. The system of claim 1, comprising:
a badge comprising the second device, the badge assigned to an entity and configured to assist in tracking actions associated with the entity.

8. The system of claim 1, comprising:
a first omnidirectional antenna structure configured to transmit the first message; and
a second omnidirectional antenna structure configured to transmit the second message.

9. The system of claim 1,
the first transceiver configured to transmit the first message responsive to a determination that a first signal strength of the first data packet exceeds a first signal strength threshold; and
the second transceiver configured to transmit the second message responsive to a determination that a second signal strength of the second data packet exceeds a second signal strength threshold.

10. The system of claim 1,
the second device configured to:

determine a first signal strength, wherein the first data packet comprises a first received signal strength indicator (RSSI) indicative of the first signal strength; and determine a second signal strength, wherein the second data packet comprises a second RSSI indicative of the second signal strength;

the first transceiver configured to transmit the first message responsive to a determination that the first RSSI is greater than a first RSSI threshold; and the second transceiver configured to transmit the second message responsive to a determination that the second RSSI is greater than a second RSSI threshold.

11. A system, comprising:

a first device, associated with a first identification number, configured to:

detect a first event;

after detecting the first event, receive a first data packet from a second device, the first data packet comprising a second identification number associated with the second device; and transmit a first message to a data processing station, the first message comprising the first identification number and the second identification number; and a third device, associated with a third identification number, configured to:

detect a second event;

after detecting the second event, receive a second data packet from the second device, the second data packet comprising the second identification number; and transmit a second message to the data processing station, the second message comprising the second identification number and the third identification number.

12. The system of claim 11, comprising:

the data processing station configured to:

determine a first time associated with the first data packet;

determine a second time associated with the second data packet;

generate a time-length of an action based upon an evaluation of the first time and the second time; and determine compliance with a protocol by comparing the time-length of the action with a time-limit associated with the protocol.

13. A method of a first device associated with a first identification number comprising:

detecting a first event;

after detecting the first event, transmitting a first inquiry in a first direction to a second device;

after transmitting the first inquiry in the first direction, receiving a first data packet from the second device, the first data packet comprising a second identification number associated with the second device; and transmitting a first message to a data processing station, the first message comprising the first identification number associated with the first device and the second identification number associated with the second device.

14. The method of claim 13, the detecting the first event comprising receiving at least one of an indication of motion at a first location or an indication of a direction of motion at the first location from a first infrared sensor; and at least one of the indication of motion at the first location or the indication of the direction of motion at the first location indicative of an entity entering a room.

15. The method of claim 13, the second device comprising a badge assigned to an entity and configured to assist in tracking actions associated with the entity.

16. The method of claim 13, the data processing station configured to generate a time-length of an action based upon an evaluation of the first message and a second message.

17. The method of claim 13, the first message transmitted to the data processing station using a first omnidirectional antenna structure of the first device.

18. The method of claim 13, the detecting the first event comprising receiving at least one of an indication of motion at a first location or an indication of a direction of motion at the first location from a first infrared sensor; and at least one of the indication of motion at the first location or the indication of the direction of motion at the first location indicative of an entity leaving a room.

19. The method of claim 13, the detecting the first event comprising receiving at least one of a first indication of motion at a first location or a first indication of a first direction of motion at the first location from a first infrared sensor; and at least one of the first indication of motion at the first location or the first indication of the first direction of motion at the first location indicative of an entity entering a room.

20. The method of claim 13, comprising:

detecting a second event;

after detecting the second event, transmitting a second inquiry in the first direction to a third device;

after transmitting the second inquiry in the first direction, receiving a second data packet from the third device, the second data packet comprising a third identification number associated with the third device; and transmitting a second message to the data processing station, the second message comprising the first identification number associated with the first device and the third identification number associated with the third device.

* * * * *